United States Patent
Tingley et al.

(10) Patent No.: US 6,589,054 B2
(45) Date of Patent: Jul. 8, 2003

(54) INSPECTION OF TEETH USING STRESS WAVE TIME NON-DESTRUCTIVE METHODS

(76) Inventors: Daniel A. Tingley, 6300 SW. Reservoir Ave., Corvallis, OR (US) 97333;
Kenneth Johnson, 2635 NW. Rolling Green Dr., Corvallis, OR (US) 97333

( * ) Notice: Subject to any disclaimer, the term of this patent is extended or adjusted under 35 U.S.C. 154(b) by 0 days.

(21) Appl. No.: 09/908,613

(22) Filed: Jul. 18, 2001

(65) Prior Publication Data

US 2002/0012897 A1 Jan. 31, 2002

Related U.S. Application Data

(60) Provisional application No. 60/219,217, filed on Jul. 18, 2000.

(51) Int. Cl.$^7$ ................................................. A61C 5/00
(52) U.S. Cl. ...................................................... 433/215
(58) Field of Search ........................... 433/215, 25, 29; 600/437

(56) References Cited

U.S. PATENT DOCUMENTS

| | | | | |
|---|---|---|---|---|
| 5,115,813 A | * | 5/1992 | Ylander et al. ............. | 600/437 |
| 5,874,677 A | * | 2/1999 | Bab et al. ................... | 433/215 |
| 6,030,221 A | * | 2/2000 | Jones et al. ................ | 433/215 |

* cited by examiner

Primary Examiner—Kevin Shaver
Assistant Examiner—Melba Bumgarner
(74) Attorney, Agent, or Firm—Chernoff, Vilhauer, McClung & Stenzel, LLP

(57) ABSTRACT

A method and device using stress waves for dental examination. According to the method, the dental structure (such as a tooth) under examination is subjected to a stress (acoustic) wave. The stress wave propagates through the dental structure and is received on the other side. From the analysis of the transmission time and/or the resulting waveform, diagnostic information results as to the presence of dental disease such as dental caries that may be present on the tooth surface under dental restorations such as fillings or metal crowns. According to the invention, the stress wave is generated by a suitable transducer, coupled to the dental structure through a transmission medium, propagates through the dental structure, coupled through another transmission medium, received by a acousto-electric transducer, and analyzed by suitable electronic means.

96 Claims, 15 Drawing Sheets

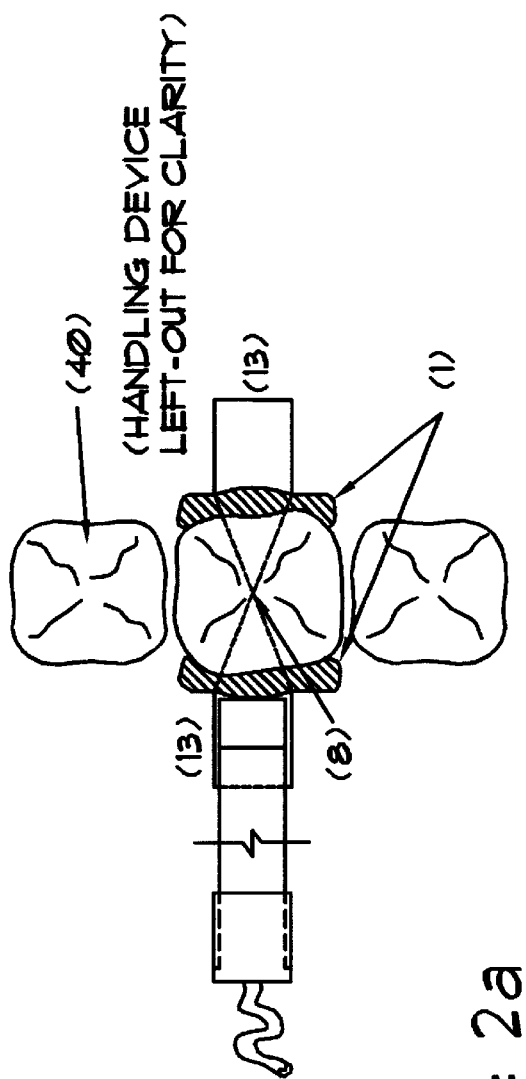
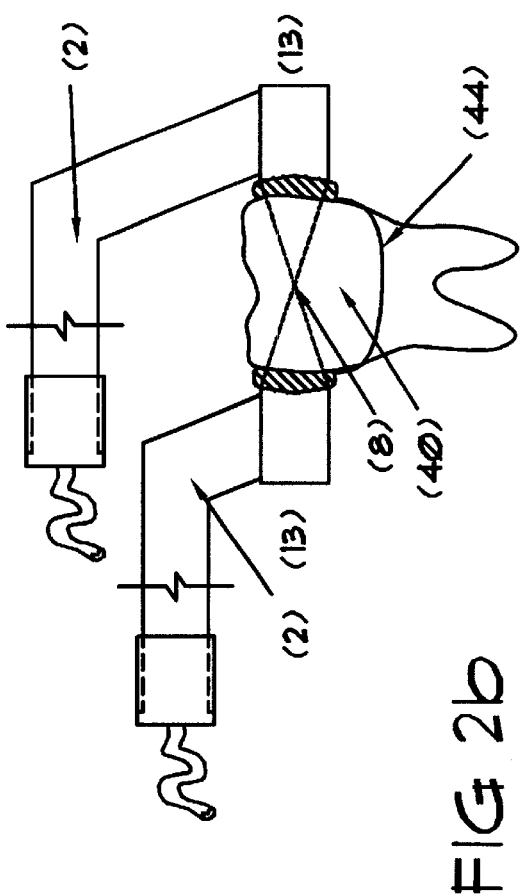
FIG 2a
FIG 2b

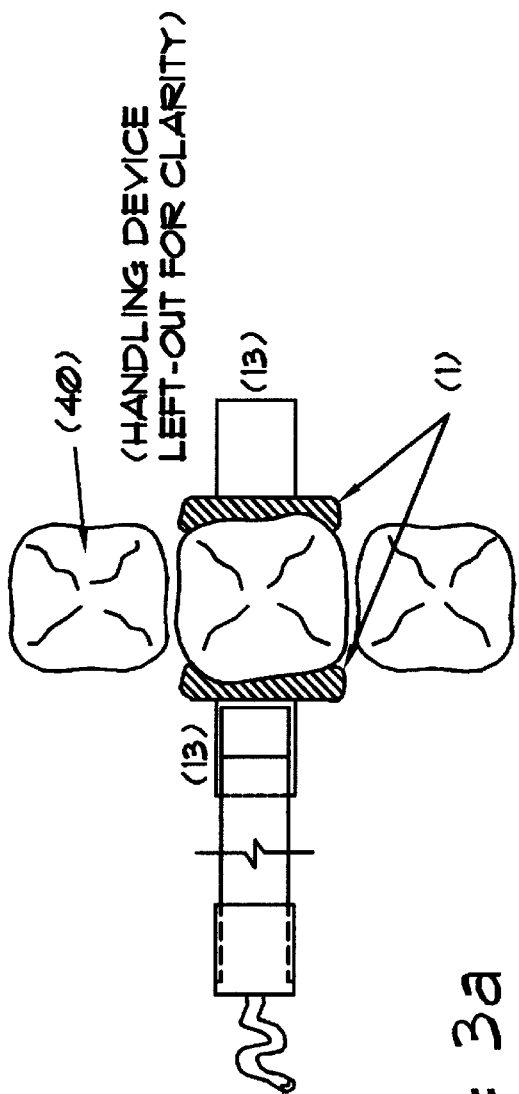
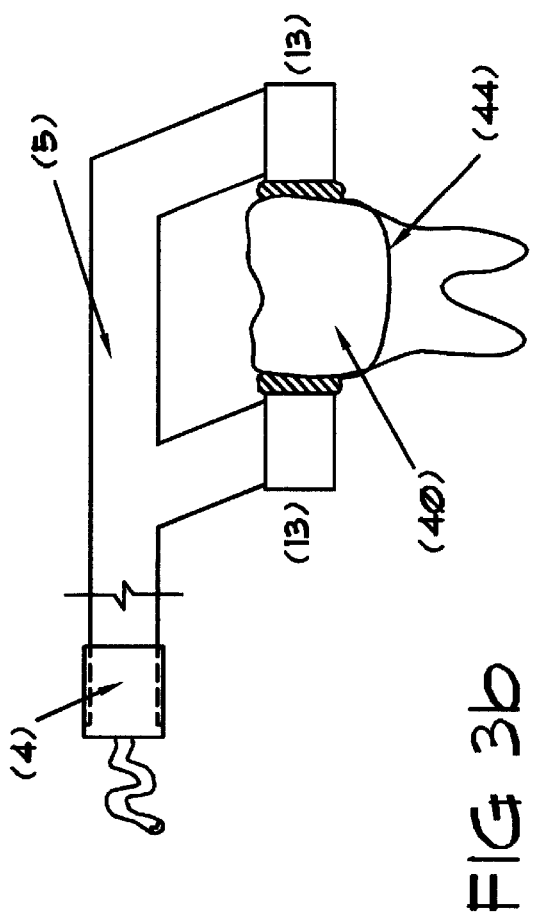

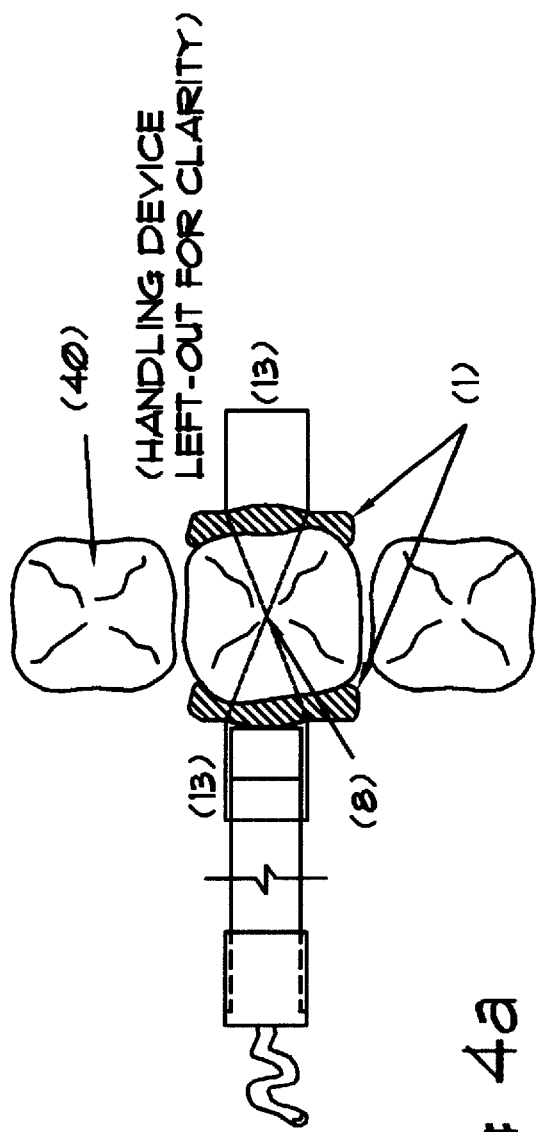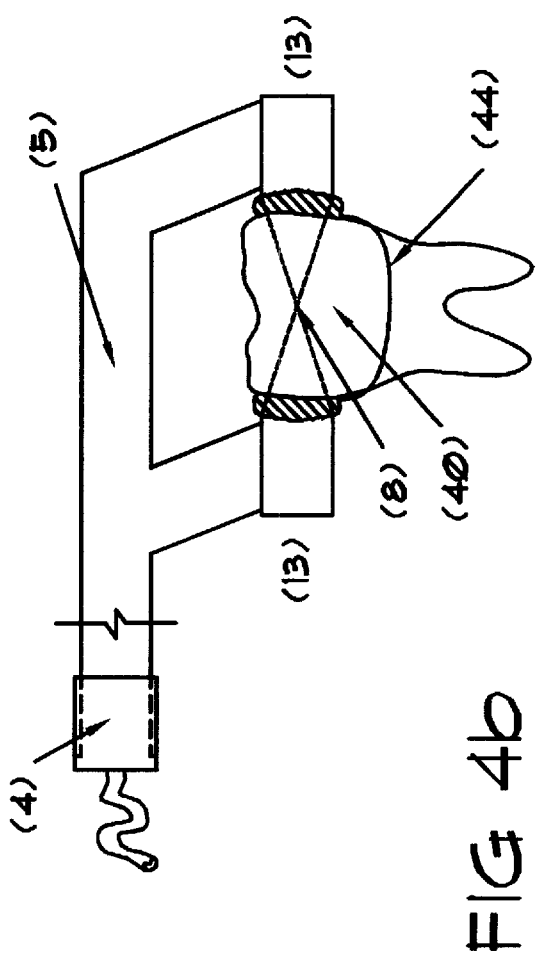
FIG 4a
FIG 4b

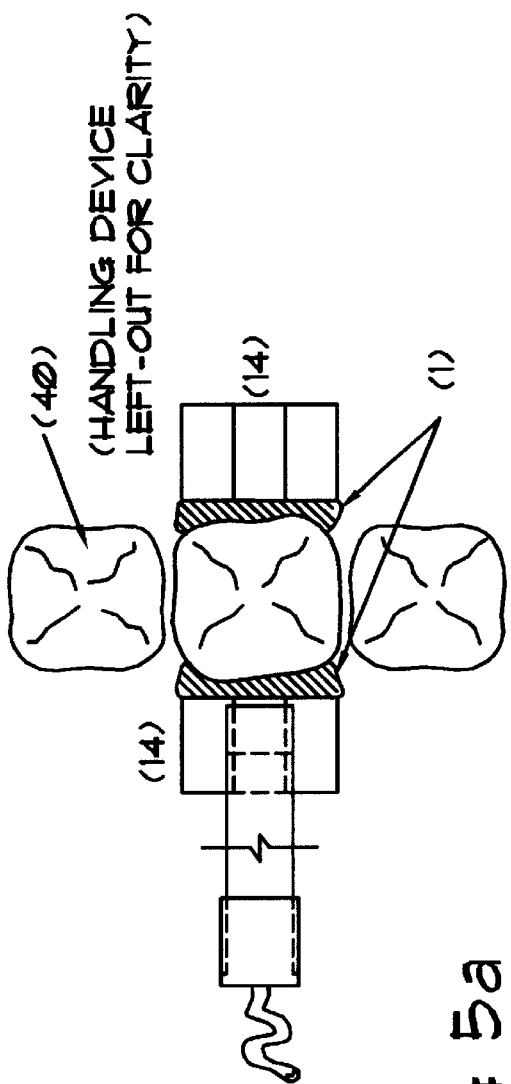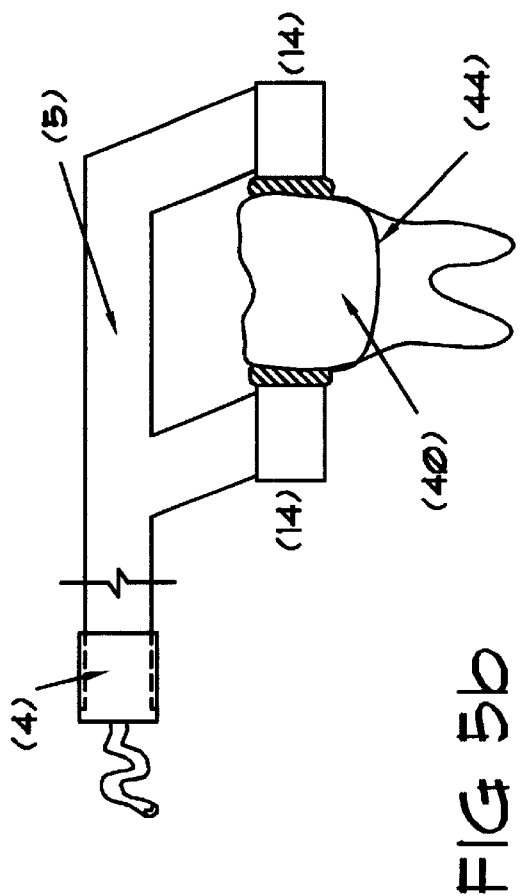
FIG 5a
FIG 5b

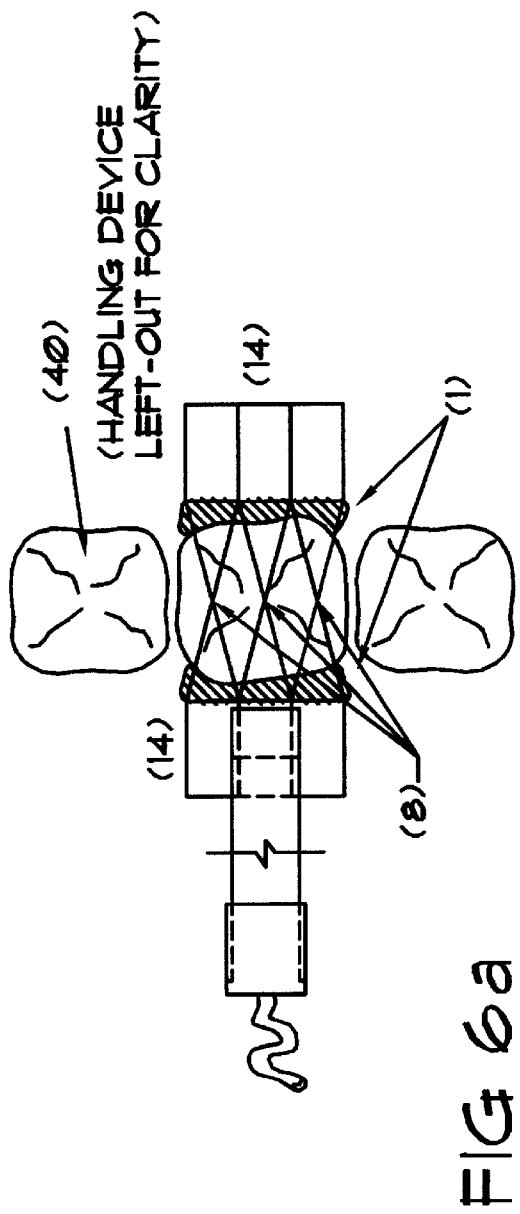
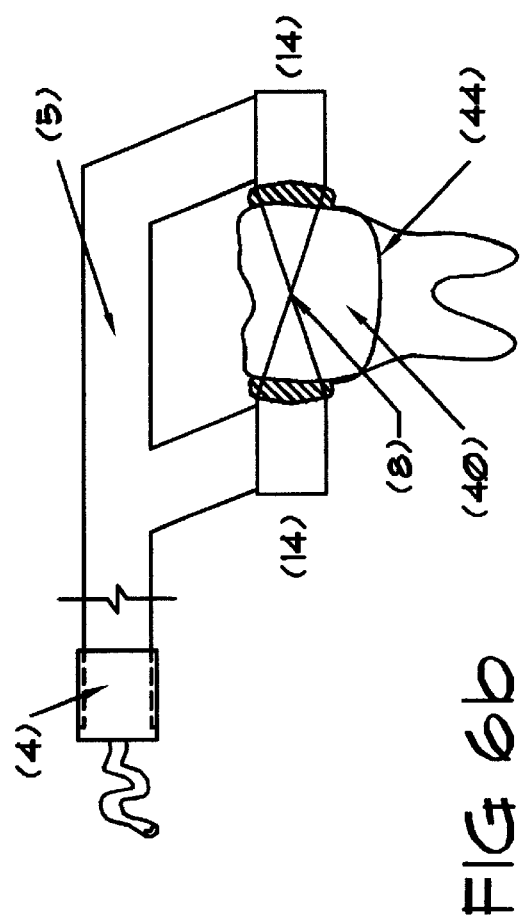
FIG 6a
FIG 6b

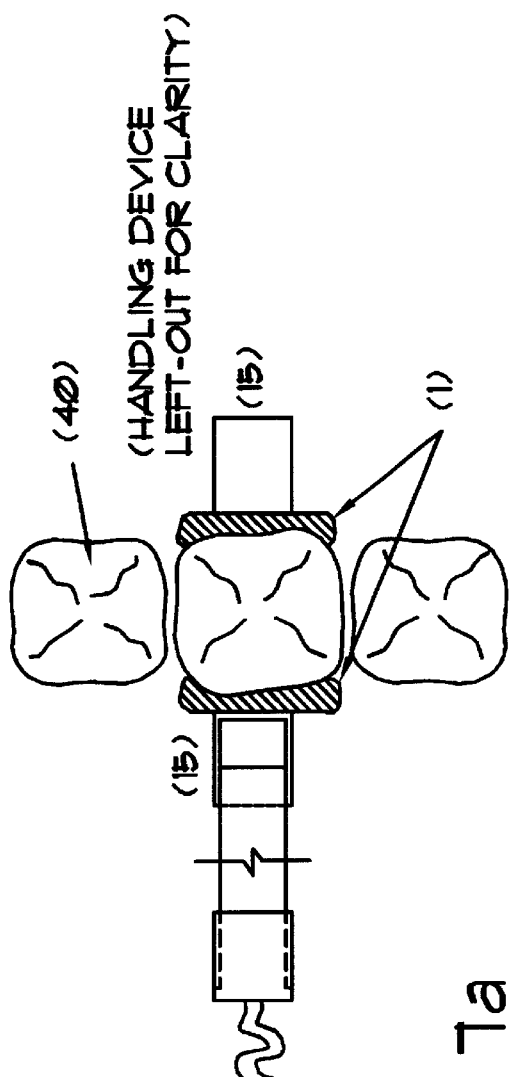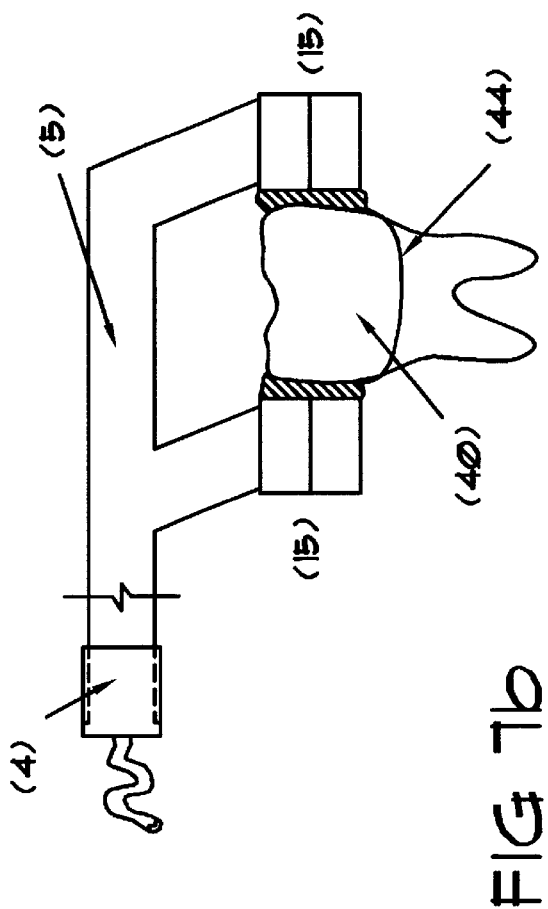

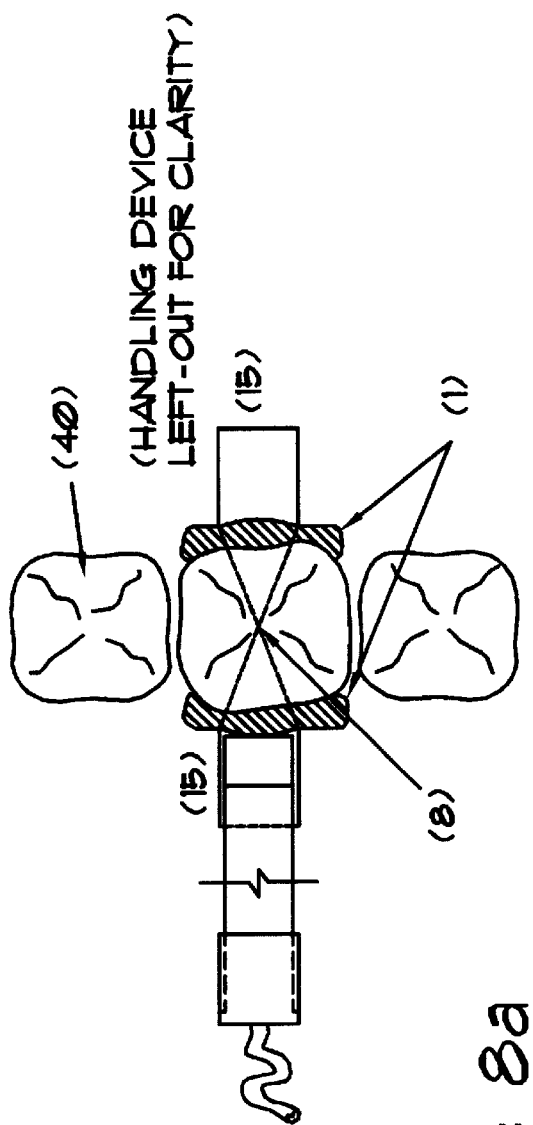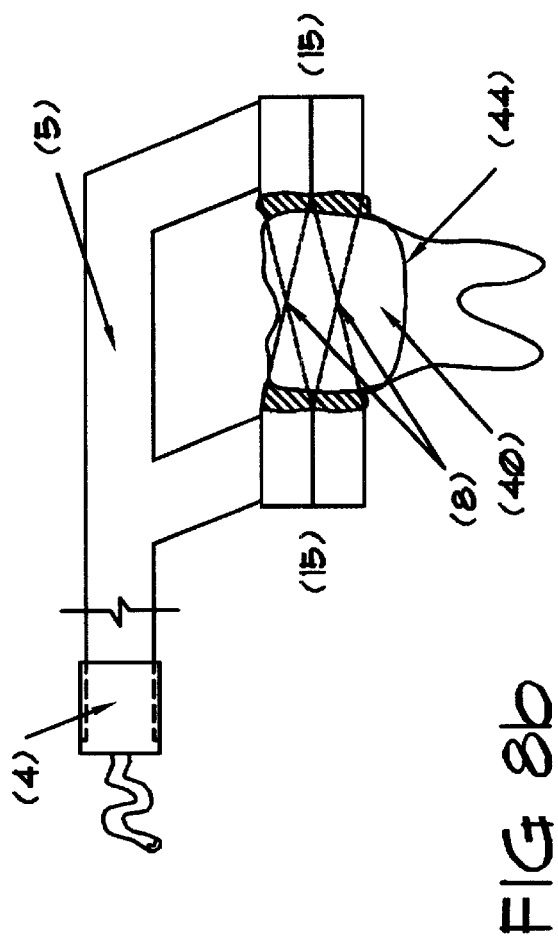

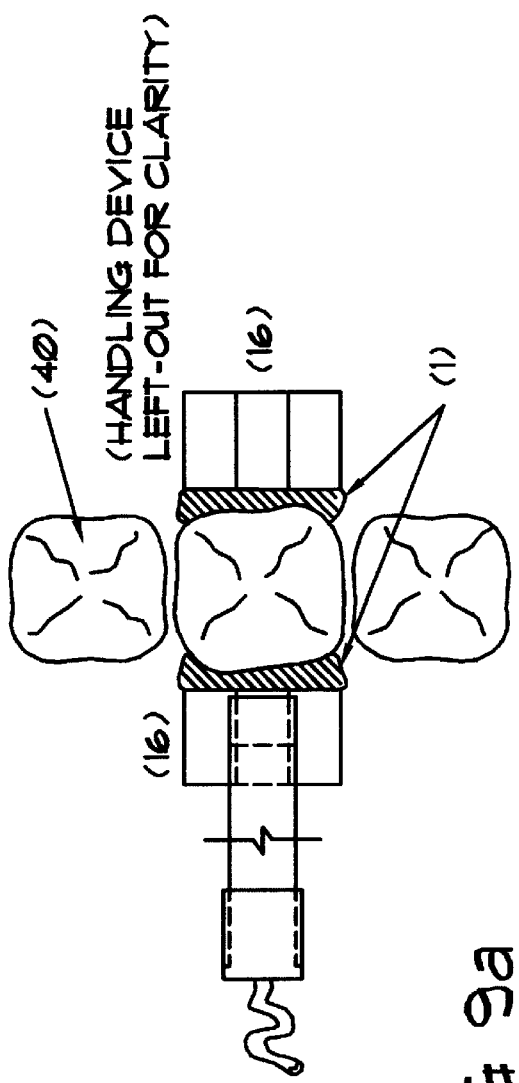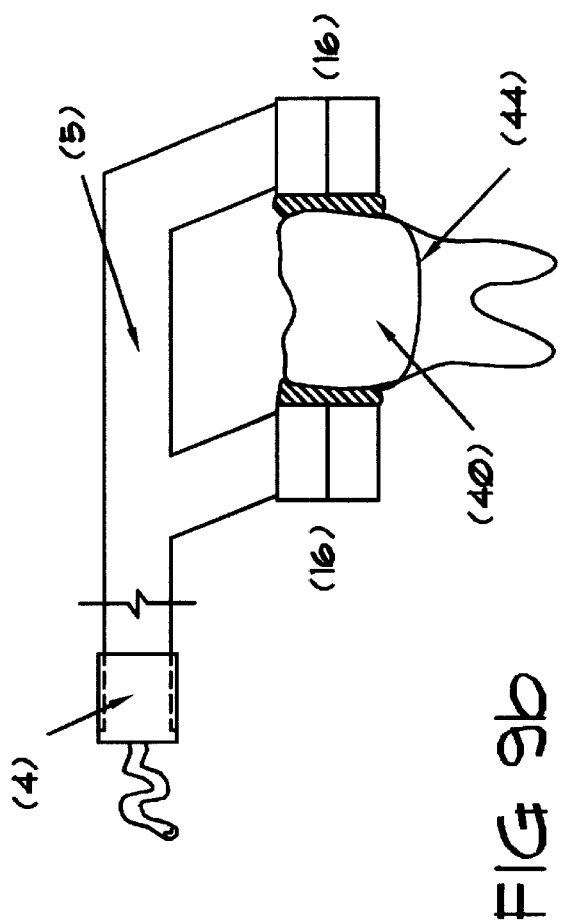
FIG 9a
FIG 9b

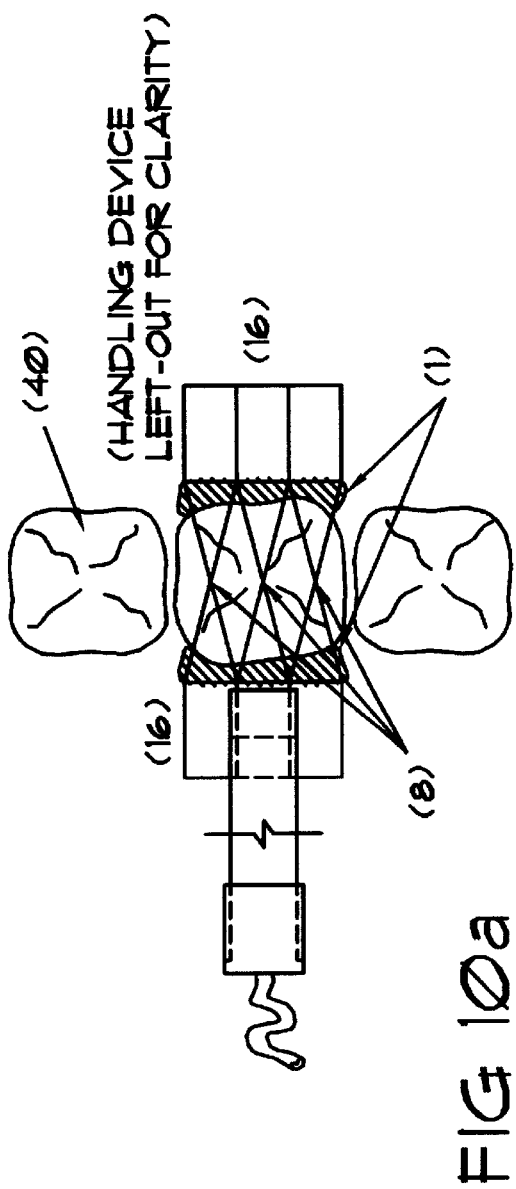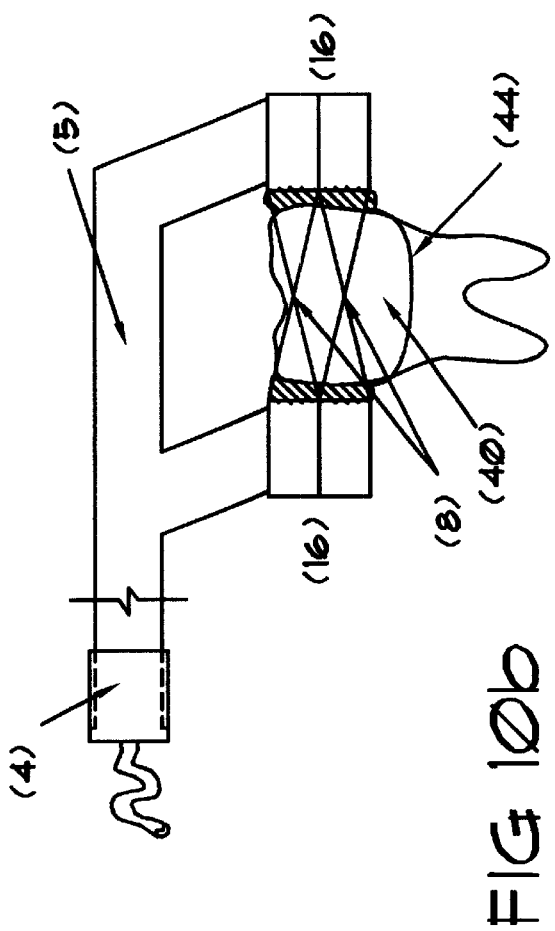
FIG 10a
FIG 10b

INSPECTION OF TEETH USING STRESS WAVE TIME NON-DESTRUCTIVE METHODS

This application claims benefit of No. 60/219,217 filed Jul. 18, 2000.

The invention relates to the non-invasive ultrasonic diagnosis of lesions on tooth surfaces or under dental restorations such as gold crowns and other dental restorations. The invention further relates to the non-invasive ultrasonic diagnosis of lesions on interproximal tooth surfaces and/or interproximal areas of dental restorations such as gold crowns and other dental restorations. The invention also relates to the non-invasive ultrasonic diagnosis of periodontal disease. Tooth lesions diagnosed could be enamel caries, dentinal caries and cracks in the tooth. Similarly, periodontal disease diagnosed could be gingivitis and periodontitis. In particular, the invention relates to ultrasonic stress waves imparted through the tooth (transmitted from one transducer through the tooth, and/or gum and bone to a second receiving transducer) or through a dental restoration for the detection of said lesions.

BACKGROUND OF THE INVENTION

Non-destructive material evaluation is the identification of physical and mechanical properties of a piece of material without altering its end-use capabilities. One effective technique used to provide accurate information pertaining to the material properties is ultrasonic Stress Wave Timing. Stress waves, for the purpose of this patent, are the propagation of stresses distributed longitudinally through material. Wavelength can encompass any range. The preferred embodiment is between ten and thirty megahertz. As indicated, stress wave can be an ultrasonic wave pulse. The basic principle of stress wave timing is to use a stress wave to measure the speed of sound transmission by recording the time it takes to pass through material and/or attenuation of induced stress wave. The speed with which sound waves travel through a material is dependent upon the materials properties. The transmission of sound through materials and the related rates of travel and attenuations is a well-understood art. All of the above cited U.S. patents, other than one (U.S. Pat. No. 5,570,182), have used a related but different method of evaluating materials with ultrasound. They have looked at the ultrasound Pulse-Echo that is returned from structures or boundaries in the tooth being evaluated, that is they use an ultrasonic transducer to transmitted a ultrasound pulse into the tooth and then used the same transducer, or another very close to it, to receive the reflected energy, the echo of that pulse, off internal layers or other structures within the tooth they are looking into. U.S. Pat. Nos. 5,874,677, 6,162,177 and 6,190,318 transmit surface (Rayleigh) waves and these patents only look for the pulse-echo from this surface wave. They do not look through the tooth; they look around the outer surface of the tooth, to diagnose carious lesions. U.S. Pat. No. 5,570,182 uses light instead of sound as a medium to evaluate materials. Many articles have been published on the use of Pulse-Echo ultrasound in teeth also. (Ultrasonic Pulse-Echo Measurements in Teeth. FE. Barber, S. Lees, R. R. Lobene. Archs oral Biol., Vol. 14, 745–760, 1969), (Observation of Internal Structures of Teeth by Ultrasonography. G. Baum, I. Greenwood, S. Slawski, R. Smirnow. Science, Vol. 139, 495–496, 1962.

According to prior art, sound in dental materials travels at different speeds according to the material it is passing through. The slowest is the tooth's pulp section, which has sound transmission characteristics very similar to water (Examination of the Contents of the Pulp Cavity in Teeth. G. Kossoff, C. J. Sharpe. Ultrasonic, 77–83, 1966), next is dentine at approximately four times faster. The fastest is in enamel at about six times faster than water (Determination of Ultrasonic Velocity in Human Enamel and Dentine. S. Y Ng, P. A. Payne, N. A. Cartledge, M. W. J. Ferguson. Archs oral Biol., Vol. 34, No. 5, 341–345, 1988). Dental caries, in general, would have a different transmission time, the time it takes for the stress (acoustic) wave to travel from the transmitting transducer to the receiving transducer, so the location and severity of material change (caries) can be found easily and quickly by recording multiple transmission times over an area. By using oscilloscopes, or other measuring or recording devices, transmission time, wave attenuation, transit times and wave shape, thus time and speed, can be recorded and evaluated. The sequence of transit times can be mapped onto the path taken by the receive and transmit transducer pairs as they are mechanically or electronically translated about the tooth. The resulting map can be thought of as an image of the shortest times taken by the stress wave through that region of the tooth defined by the transducer locations. Regions of anomalous transit times are interpreted as regions of dental caries or some other defect in the tooth structure. Mapping is the preferred embodiment of imaging, of the material (tooth and gums) that can be used to diagnose lesions such as enamel caries, dentinal caries and cracks in the tooth. (Development and Application of an Ultrasonic Imaging System for Dental Diagnosis. H. Fukukita, T. Yanco, A. Fukumoto, K. Sawada, T. Fujimasa, and I. Sciaenidae. Journal Of Clinical Ultrasound No. 13, 597–600, October 1985).

In particular, the invention relates to ultrasonic stress waves imparted through the tooth or dental restoration for the detection of these lesions. Periodontal disease, such as gingivitis, periodontitis can be diagnosed also.

Dental caries (dental cavities or tooth decay) is a disease manifested by local demineralization of the enamel and dentine of the tooth caused by dental plaque. The demineralization process progresses from the outer enamel surface of the tooth through the entire thickness of the enamel and into the dentine. Caries lesions of occlusal (biting surface), buccal (cheek side) and lingual (tongue side) surfaces can be diagnosed by mechanical probing and/or visual inspection. It is difficult or impossible to find small and medium size lesions of interproximal surfaces hidden by the gums and/or adjacent teeth. These can usually only be found with dental X-rays (radiographs). Although the use of bitewing radiographs is often used as a tool in the diagnosis of proximal caries lesions, this method has several weaknesses because of its relative insensitivity and user dependence in terms of technical skill and interpretation (Waggoner W., F. Crall J. J. Quintessence International 11/1984: 1163–1173). It should be noted that bitewing radiographs have a high proportion of X-rays taken in the dental office. This is contrary to current trends in safety standards that support every effort aimed at reducing the exposure to ionizing irradiation.

Caries lesions not adjacent to a dental restoration on a tooth surface site are known as primary caries, while caries lesions in contact with a dental restoration at the tooth surface are known as secondary caries. Secondary caries would be caries next to a filling or under a gold crown.

In conventional methods X-ray machines are used for the examination of dental tissue. Also apparatuses for measuring dense tissue by means of ultrasound are known in the art. The publication (Development and Application of an Ultrasonic Imaging System for Dental Diagnosis. H. Fukukita, T. Yanco, A. Fukumoto, K. Sawada, T. Fujimasa, and I. Sciaenidae. Journal Of Clinical Ultrasound No. 13, 597–600, October 1985), describes an ultrasound measurement method for examining teeth.

Because of the health hazards caused by high power levels required for x-ray fluoroscopy, it is impossible to obtain real-time information. More importantly the power level of X-rays used in dental offices cannot penetrate metal crowns used in tooth restoration. This means secondary caries and cracks in the tooth under the crown cannot be diagnosed.

In stress (acoustic) waves ultrasonic and sonic refer only to the frequency of excitation, ultrasonic being frequencies above 20 KHz used to impart a wave into the material. The velocity of a stress wave is dependent on the material properties only, not the frequency of excitation. All commercially available timing units give comparable results if calibrated and operated according to the manufacturers direction.

In existing art of ultrasonic procedure, an electrical device known as a pulser/receiver generates an electrical pulse to a transducer that changes the electrical pulse into an ultrasonic pulse (stress wave). The transducer, in turn, directs the ultrasonic pulse to any desired surface where it is transmitted thru that object and out the other side. The ultrasonic pulse received by a second transducer, the receiving transducer, is converted by said transducer to an electrical pulse for display on the cathode ray tube of the oscilloscope or other data processing equipment.

Ultrasonic devices such as transducers can be coupled to an object by air or water. While water is effective it is hard to use in an open environment such as a mouth. Transducers are more effective when used with a coupling medium such as acoustical gel or ultrasonic coupling devices. An ultrasonic coupling device could be a bladder made of an ultrasonic conducting membrane and filled with an ultrasonic conducting material like silicon, water, oil, etc. Focused ultrasonic transducers in prior art refer to transducer designed to concentrate ultrasonic sound waves to a spot at the focal length of the given transducer. This spot is usually much smaller in diameter than the face of the transducer. This focusing effect is the same for transmitting and receiving. By focusing a given transducer there is an increase in gain in the ultrasonic signal and an increase in the resolution of the device often to parts of a millimeter.

We propose the use of two classes of arrays of stress (acoustic) transducers. The first class represents one-dimensional arrays where the transducers are arranged in either a straight line (a linear array) on a curved line (curvilinear array). The second class represents two-dimensional arrays where the transducers are arranged on either a flat rectilinear grid or on a curved grid.

A phased array is an array of transducers and electronic circuitry that produce a focused receive and/or transmit stress (acoustic) beam. It functions in a manner similar to phased array RADAR.

SUMMARY OF INVENTION

It is an object of the invention to provide a method of detecting dental lesions under a gold crown or other dental restoration.

It is further an object of the invention to provide a method of detecting dental lesions under the gum line.

It is further an object of the invention to provide a method of detecting dental lesions in the interproximal area.

It is further an object of the invention to provide a non-invasive method of detecting or diagnosing periodontal disease.

It is also an object of the invention to be able to provide real-time ultrasonic tomography, a form of mapping or imaging, of a tooth and surrounding gum and bone material.

The foregoing and other objectives, features, and advantages of the invention will be more readily understood upon consideration of the following detailed description of the invention, taken in conjunction with the accompanying drawings.

BRIEF DESCRIPTION OF DRAWINGS

FIG. 1 illustrates the main features of the first embodiment of the transducer system. It shows two ultrasonic transducers placed on opposite sides of a tooth. There would be an ultrasonic coupling device or material between the tooth and the transducer on each side of the tooth.

FIG. 2 illustrates the main features of the second embodiment of the transducer system. It shows two focused ultrasonic transducers placed on opposite sides of a tooth. There would be an ultrasonic coupling device or material between the tooth and the transducer on each side of the tooth; FIG. 2(a) is a top view. FIG. 2(b) is a side view showing handling devices to hold the transducers in place.

FIG. 3 illustrates the main features of the third embodiment of the transducer system. It shows two ultrasonic transducers placed on opposite sides of a tooth. There would be an ultrasonic coupling device or material between the tooth and the transducer on each side of the tooth; FIG. 3(a) is a top view. FIG. 3(b) is a side view showing a laterally traversing fixture to hold the transducers.

FIG. 4 illustrates the main features of the fourth embodiment of the transducer system. It shows two focused ultrasonic transducers placed on opposite sides of a tooth. There would be an ultrasonic coupling device or material between the tooth and the transducer on each side of the tooth; FIG. 4(a) is a top view. FIG. 4(b) is a side view showing a laterally traversing fixture to hold the transducers.

FIG. 5 illustrates the main features of the fifth embodiment of the transducer system. It shows a horizontal array of ultrasonic transducers placed on opposite sides of a tooth. Each array would have two or more transducers. The transducers would be all on the same horizontal plane. There would be an ultrasonic coupling device or material between the tooth and the transducer on each side of the tooth; FIG. 5(a) is a top view. FIG. 5(b) is a side view showing a possible fixture to hold the horizontal array transducers.

FIG. 6 illustrates the main features of the sixth embodiment of the transducer system. It shows horizontal array of focused ultrasonic transducers placed on opposite sides of a tooth. Each array would have two or more transducers. The transducers would be all on the same horizontal plane. There would be an ultrasonic coupling device or material between the tooth and the transducer on each side of the tooth; FIG. 6(a) is a top view. FIG. 6(b) is a side view showing a possible fixture to hold the horizontal arrays of transducers.

FIG. 7 illustrates the main features of the seventh embodiment of the transducer system. It shows vertical array of ultrasonic transducers placed on opposite sides of a tooth. Each array would have two or more transducers. The transducers would be all on the same vertical plane. There would be an ultrasonic coupling device or material between the tooth and the transducer on each side of the tooth; FIG. 7(a) is a top view. FIG. 7(b) is a side view showing a laterally traversing fixture to hold the vertical array transducers.

FIG. 8 illustrates the main features of the eighth embodiment of the transducer system. It shows a vertical array of focused ultrasonic transducers placed on opposite sides of a tooth. Each array would have two or more transducers. The transducers would be all on the same vertical plane. There would be an ultrasonic coupling device or material between the tooth and the transducer on each side of the tooth; FIG. 8(a) is a top view. FIG. 8(b) is a side view showing a laterally traversing fixture to hold the vertical arrays of transducers.

FIG. 9 illustrates the main features of the ninth embodiment of the transducer system. It shows a horizontal and vertical array of ultrasonic transducers placed on opposite sides of a tooth. Each array would have two or more transducers. The each row of transducers would be all on the same horizontal or vertical plane respectively. There would be an ultrasonic coupling device or material between the tooth and the transducer on each side of the tooth; FIG. 9(a) is a top view. FIG. 9(b) is a side view showing a laterally traversing fixture to hold the arrays of transducers.

FIG. 10 illustrates the main features of the tenth embodiment of the transducer system. It shows a horizontal and vertical array of focused ultrasonic transducers placed on opposite sides of a tooth. Each array would have two or more transducers. The each row of transducers would be all on the same horizontal or vertical plane respectively. There would be an ultrasonic coupling device or material between the tooth and the transducer on each side of the tooth; FIG. 10(a) is a top view. FIG. 10(b) is a side view showing a laterally traversing fixture to hold the arrays of transducers.

DETAILED DESCRIPTION OF THE PREFERRED EMBODIMENT

The present invention relates to a process of using through wave time of flight and other wave characteristics to detect dental lesions 41 in a tooth 40. For our purposes, wave characteristics are the amplitude, phase, spatial position, timing, and general shape of the stress (acoustic) wave. A transducer system comprising of a transmitting ultrasonic transducer that transmits an ultrasonic pulse (stress wave) through dental material such as a tooth 40 or gum 45, and a receiving ultrasonic transducer that receives the resulting ultrasonic pulse from the opposite side of the system and the resulting information, such as time of arrival of the stress wave and amplitude is processed. The system can include two or more transducers.

Figure 15:
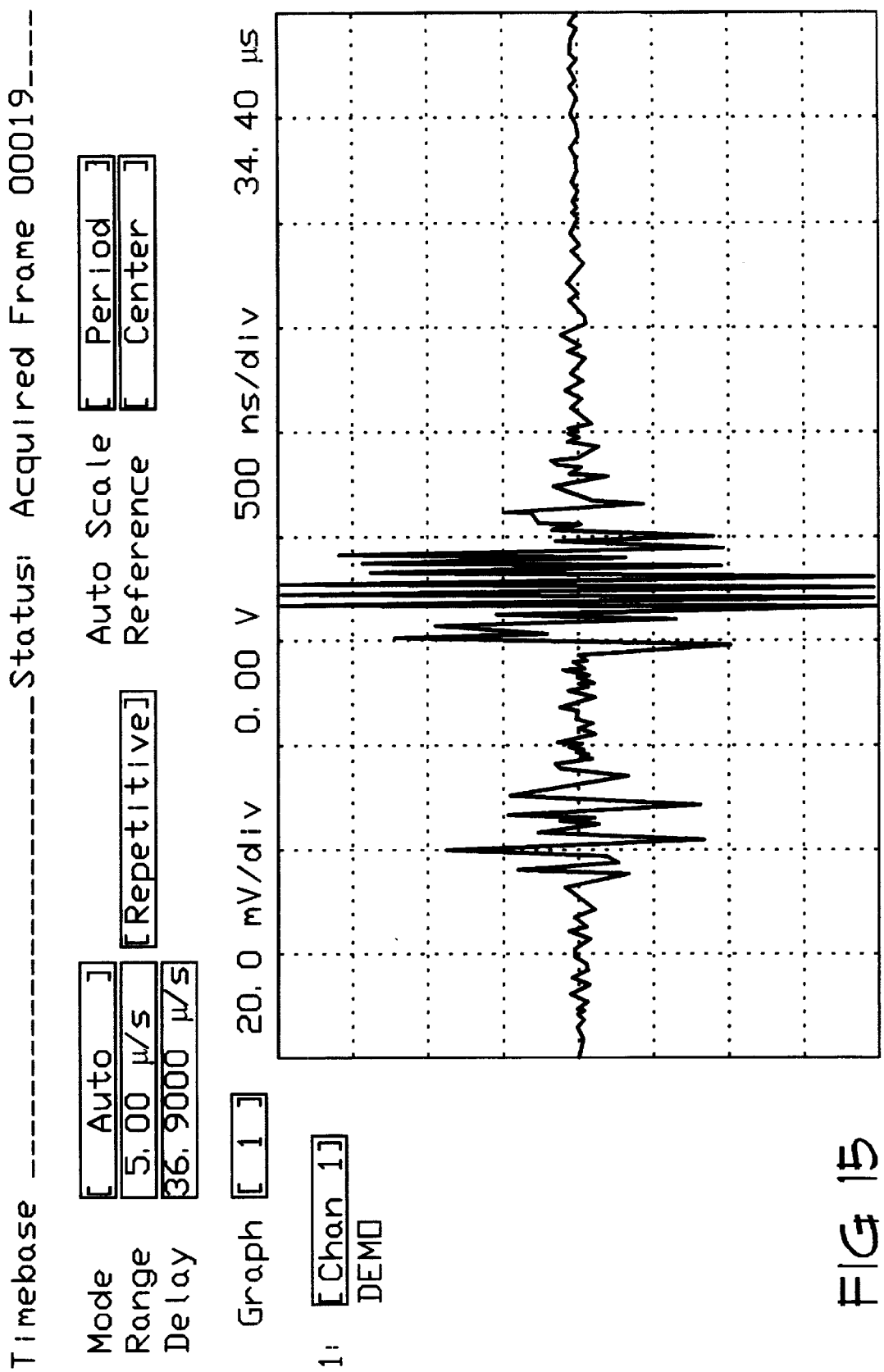
FIG. 15 illustrates a sample of received waveform as seen by a single receiving transducer.

Due to the many possible paths through the tooth, the stress (acoustic) wave transmitted by the transmit transducer will result in many waves, separated in time, at the receive transducer. These many waves combine to produce a composite stress wave at the transducer that results in a complex electrical signal whose amplitude and phase directly corresponds to the composite stress (acoustic) wave (FIG. 15).

In principle, collecting such composite wave signals from all angles and positions through the tooth allows one to tease out all the paths taken by the transmit stress wave. Knowledge of these paths allows one to precisely locate and extent of every structure (and defect) of the tooth. Such a process is very complex and hence costly to implement.

Much structural information can be obtained by limiting the analysis of the composite signal to the transmission time of the shortest path, in time, of the stress wave. This analysis is well known in the field of non-destructive testing of wood structures.

In wood structures non-destructive material evaluation is the identification of physical and mechanical properties of a piece of material without altering its end-use capabilities. A technique used to provide accurate information pertaining to the material properties is stress wave timing. This basic principle of stress wave timing is to measure the speed of sound transmission time and/or attenuation of induced stress (acoustic) waves. The speed with which sound waves travel through a material is dependent upon the materials properties. Decayed regions, in general, would have a different transmission time so the location and severity of material change (decay) can be found easily and quickly by recording multiple transmission times over an area. Measuring wave attenuation is a variant of the speed measure in that the energy dissipation as a wave travels through the material is recorded. The wave attenuation measures can also provide a "map" of the material that defines the magnitude and extent of any decay.

The transit (transmission) time of the shortest path stress (acoustic) signal doubly useful as it is also the easiest to detect. It is easiest to detect because it is the first signal to arrive at the receive transducer. Nevertheless, there is some complexity in the choice of method used to detect the transmission time of the first signal.

One preferred method known in the art of wood testing is to set the level of an electronic threshold detector such that a stop signal is generated when the receive signal exceeds some preset level. This level is set just above the noise level of the instrumentation. Thus, and signal that exceeds this level is due to the stress signal. The transmission time is measured by a timer that begins with the transmit start (initiation) signal and stops at the first stop signal produced by the threshold detector.

Another preferred method uses an electronic peak detector to create the stop signal. The peak detector is set to create a stop pulse at each peak of the stress (acoustic) signal. Like the threshold detector, the peak detector will produce numerous stop signals but the transmission timer will always stop at the first stop signal, thus giving rise to the transmission time of the shortest path stress signal.

Yet another preferred method is to use either detector on the envelope of the received signal. Like the detectors, the creation of the envelope of the stress signal is known in the art. The first stop signal so produced will be at the point in time when the threshold level or the peak of the envelope of the stress signal has been reached. The advantage of using the envelope of the signal is that the resultant transit time is the transmission time of the energy in the stress signal.

Another preferred method uses a peak detector that works on the first derivative of envelope of the stress signal. Like the peak detector, the creation of the fist derivative of the stress signal is known in the art. The first stop signal so produced will be at the point, in time, when the slope of the shortest stress signal's energy is at its maximum.

Another preferred method uses a peak or threshold detector on the correlation signal produced by correlation of the received stress signal with the conjugate of the transmitted stress signal. Such correlation process is known in the art. The fist stop signal will be at the point, in time, when the received signal first matches the transmitted signal. This method allows the use of more complex transmit stress signals which in turn can increase the timing accuracy.

The present invention further relates to a process of using through wave time of flight and other wave characteristics to detect cracks in a tooth 40 comprising of a transmitting ultrasonic transducer that transmits an ultrasonic pulse (stress wave) through dental material such as a tooth 40 or gum 45, and a receiving ultrasonic transducer that receives the resulting ultrasonic pulse from the opposite side of the system and the resulting information, such as time of arrival of the stress wave and amplitude is processed. The system can include two or more transducers.

The present invention further relates to a process of using through wave time of flight and other wave characteristics to detect dental lesions 41 on interproximal tooth surfaces and/or interproximal areas of dental restorations such as gold crowns 42 and other dental restorations, comprising of a transmitting ultrasonic transducer that transmits an ultrasonic pulse (stress wave) through dental material such as a tooth 40 or gum 45, and a receiving ultrasonic transducer that receives the resulting ultrasonic pulse from the opposite side of the system and the resulting information, such as time of arrival of the stress wave and amplitude is processed. The system can include two or more transducers.

The present invention further relates to a process of using through wave time of flight and other wave characteristics to detect dental lesions 41 under gum tissue, comprising of a transmitting ultrasonic transducer that transmits an ultrasonic pulse (stress wave) through dental material such as a tooth 40 or gum 45, and a receiving ultrasonic transducer that receives the resulting ultrasonic pulse from the opposite side of the system and the resulting information, such as time of arrival of the stress wave and amplitude is processed. The system can include two or more transducers.

The present invention also relates to a process of using through wave time of flight and other wave characteristics to diagnose periodontal disease such as gingivitis, periodontitis, comprising of a transmitting ultrasonic transducer that transmits an ultrasonic pulse (stress wave) through dental material such as a tooth 40 or gum 45, and a receiving ultrasonic transducer that receives the resulting ultrasonic pulse from the opposite side of the system and the resulting information, such as time of arrival of the stress wave and amplitude is processed. The system can include two or more transducers.

Figure 1A:
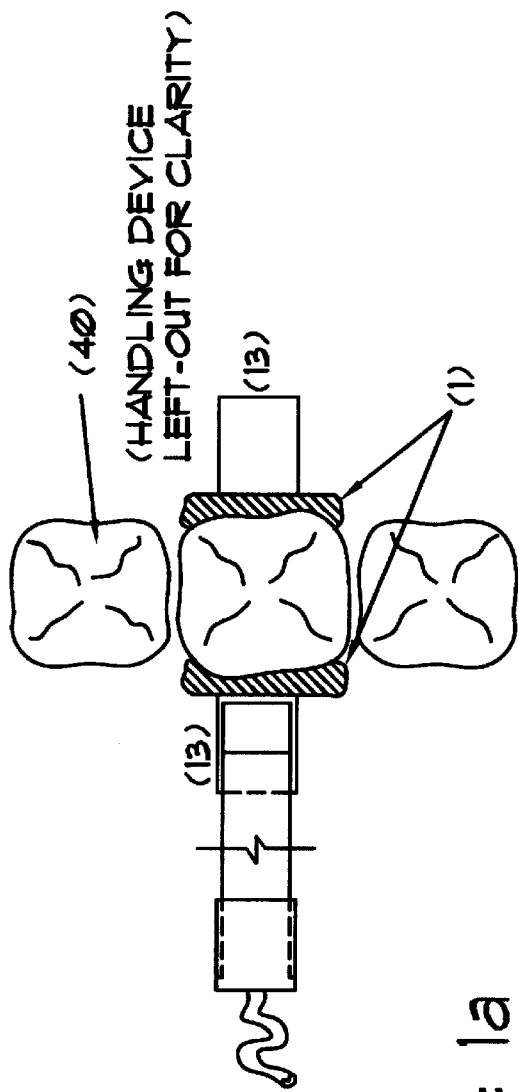
FIG. 1(a) is a top view.
Figure 1B:
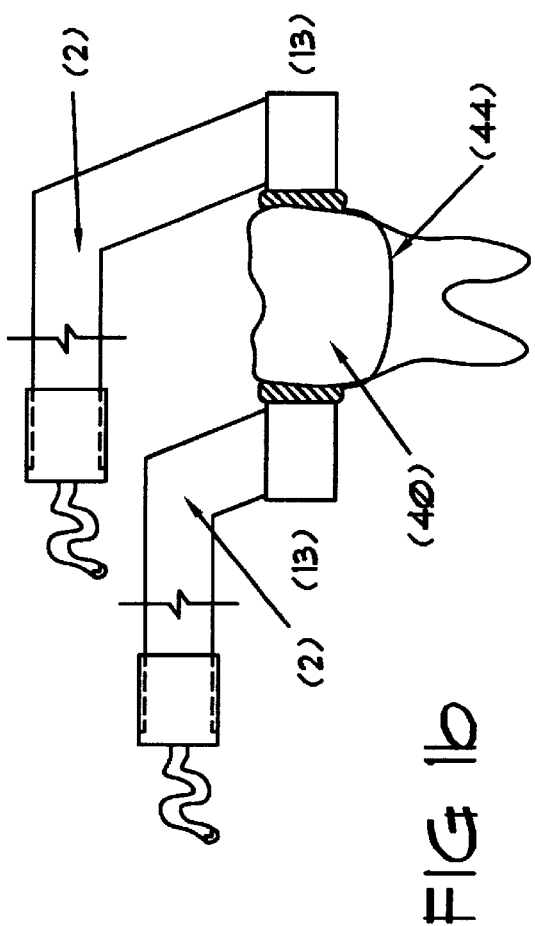
FIG. 1(b) is a side view showing handling devices to hold the transducers in place.

The first embodiment of the present invention is shown in FIG. 1. It shows the overall concept of the transducer system 13. The system is comprised of a pair of transducers placed opposite each other and in approximation to the tooth 40 to be examined. There needs to be a coupling agent or device present between the tooth 40 and the transducers. Each transducer would have handling device 2 attached to help position it.

The second embodiment of the present invention is shown in FIG. 2. It shows the overall concept of the transducer system 13. The system is comprised of a pair of focused transducers collinearly placed opposite each other and spaced apart such that their focal points 8 coincide or are near to each other. They will be placed on the opposite sides of the tooth 40 to be examined. There needs to be a coupling agent or device present between the tooth 40 and the transducers. Each transducer would have handling device 2 attached to help position it.

The third embodiment of the present invention is shown in FIG. 3. It shows the overall concept of the transducer system 13. The system is comprised of a pair of transducers placed opposite each other and in approximation to the tooth 40 to be examined. There needs to be a coupling agent or device present between the tooth 40 and the transducers. These transducers would have a connecting bridge 5 between the transducers to maintain their alignment. There could be handling device 2 attached to the arrangement of transducer system and/or connecting bridge 5 for help in positioning.

The fourth embodiment of the present invention is shown in FIG. 4. It shows the overall concept of the transducer system 13. The system is comprised of a pair of focused transducers collinearly placed opposite each other and spaced apart such that their focal points 8 coincide or are near to each other. They will be placed on the opposite sides of the tooth 40 to be examined. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The fifth embodiment of the present invention is shown in FIG. 5. It shows the overall concept of the transducer system 14. The system is comprised of a horizontal array of transducers placed opposite each other and in approximation to the tooth 40 to be examined. The arrays can be planar or curvilinear. If they are planar they should be opposite across the tooth 40. If they are curvilinear they should be on the same horizontal plane across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The sixth embodiment of the present invention is shown in FIG. 6. It shows the overall concept of the transducer system 14. The system is comprised of a horizontal array of focused transducers collinearly placed opposite each other and spaced apart such that their focal points 8 coincide or are near to each other. They will be placed on the opposite sides of the tooth 40 to be examined. The arrays can be planar or curvilinear. If they are planar they should be opposite across the tooth 40. If they are curvilinear they should be on the same horizontal plane across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The seventh embodiment of the present invention is shown in FIG. 7. It shows the overall concept of the transducer system 15. The system is comprised of a vertical array of transducers placed opposite each other and in approximation to the tooth 40 to be examined. The arrays can be planar or curvilinear. If they are planar they should be opposite across the tooth 40. If they are curvilinear they should be on the same vertical plane across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The eighth embodiment of the present invention is shown in FIG. 8. It shows the overall concept of the transducer system 15. The system is comprised of a vertical array of focused transducers collinearly placed opposite each other and spaced apart such that their focal points 8 coincide or are near to each other. They will be placed on the opposite sides of the tooth 40 to be examined. The arrays can be planar or curvilinear. If they are planar they should be opposite across the tooth 40. If they are curvilinear they should be on the same vertical plane across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The ninth embodiment of the present invention is shown in FIG. 9. It shows the overall concept of the transducer system 16. The system is comprised of a horizontal and vertical array of transducers placed opposite each other and in approximation to the tooth 40 to be examined. The arrays can be planar or curvilinear. If they are planar they should be opposite across the tooth 40. If they are curvilinear they should be on the same horizontal and vertical planes across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

The tenth embodiment of the present invention is shown in FIG. 10. It shows the overall concept of the transducer system 13. The system is comprised of a horizontal and vertical array of focused transducers collinearly placed opposite each other and spaced apart such that their focal points 8 coincide or are near to each other. They will be placed on the opposite sides of the tooth 40 to be examined. The arrays can be planar or curvilinear. If they are planar they should be opposite across the tooth 40. If they are curvilinear they should be on the same horizontal and vertical planes across the tooth 40. There needs to be a coupling agent or device present between the tooth 40 and the transducers. These transducers would have a connecting bridge 5 between the transducers to maintain their alignment. There could be handling device 4 attached to the arrangement of transducer system and/or connecting bridge 5 for help in positioning.

Figure 11:
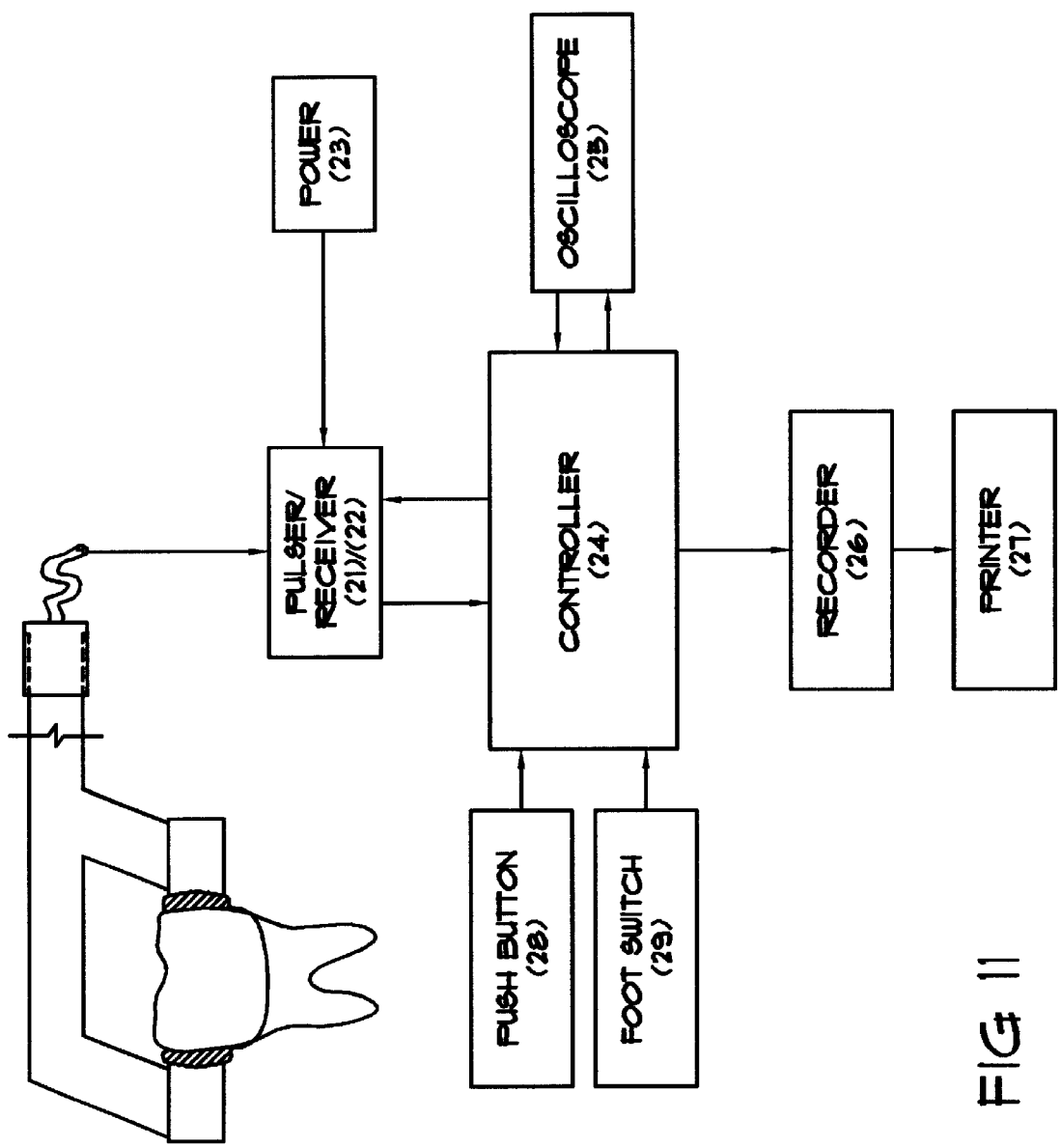
FIG. 11 illustrates the first to the fourth embodiment of the transducer system with a block diagram of peripheral electrical and/or electronic components.

In the preferred embodiment FIG. 11 shows a transducer system 13 may be interconnected to peripheral electronic and/or electrical components. This illustrates schematically one example of the relationship between said transducer system 13 and peripheral components for at least some of the corresponding embodiments of said transducer system 13. A pulser (signal generator) 21 producing a suitable electronic ultrasonic pulse is electrically connected to the transmitting transducer that is then able to impart ultrasonic stress waves through the tooth 40 as hereinbefore described. Stress waves received by the receiving transducer are converted into corresponding electrical signals that are then amplified and processed in a processor (receiver) 22.

Peripheral electronic means such as an oscilloscope 25 can be used with the processor 22 and may be used for displaying the profile of said stress waves received by said the receiving transducer 13 in a manner known in the art. Said electrical signals may also be connected to an electronic computer 31 for further analysis. The said oscilloscope 25 may typically display a receive pulse waveform (FIG. 15). The receive pulse waveform represented by the transmission time displayed on the oscilloscope 25 is formed of many parts. Transmission time is the time it takes for the stress (acoustic) wave to travel from the transmitting transducer to the receiving transducer. Due to the complex paths the stress wave can take through the various structures of the tooth 40, there is a transmission time for every possible path. The shortest path in time is not necessarily the shortest path in space. The stress wave may travel further in a higher velocity enamel layer and yet arrive sooner than the wave that travels a shorter path through the lower velocity dentine layer. Due to the many possible paths through the tooth 40, the stress wave transmitted by the transmit transducer will result in many waves, separated in time, at the receive transducer. For our purposes, transmission time represents the time it takes for the first stress wave to reach the transducer. This time represents the shorted stress (acoustic) path in time through the tooth 40. Each time the transducer system is moved, either manually, mechanically the transmission time displayed on the oscilloscope 25 will be different. With suitable analysis, a system will be able to identify dental lesions 41 and other defects by analyzing the different transmission times and the resulting waveforms. The received stress wave electrical signals may also be channeled to an electronic recording or storage device 26 for further analysis. If a electronic recording or storage device 26 is used there will be either pushbuttons 28 on the handling device 2, 4 or footswitches 29 for the transducer system that will signal the computer 31 when to record 26 the received stress wave waveform so it can be processed and/or be viewed or printed 27 latter.

We propose the use of two classes of arrays of stress (acoustic) transducers. The first class represents one-dimensional arrays 14–15 where the transducers are arranged in either a straight line (a linear array) on a curved line (curvilinear array). The second class represents two-dimensional arrays 16 where the transducers are arranged on either a flat rectilinear grid or on a curved grid.

A phased array is an array of transducers and electronic circuitry that produce a focused receive and/or transmit stress (acoustic) beam. In transmit, the electronic signals input into each transmit transducer is timed such that the resulting stress (acoustic) wave from each respective transducer will converge at a point in front of the array (the transmit focus). In receive, the electronic signals from each receive transducer is delayed such that the sum of all the delayed signals is a single signal that is maximized only when the stress (acoustic) energy emanates from a point front of the array (receive focus). By suitable timing and delay, the transmit and receive signals can be moved in a plane containing the receive and transmit arrays. Thus, the point of maximum stress (acoustic energy) and maximum stress (acoustic) sensitivity can be electronically translated laterally along the arrays, axis and in range in front of the arrays. For our purposes, overlapping the transmit and receive focus of the opposed receive and transmit arrays insures that the maximum signal will be that set of paths which travel trough the combined focus. This limits the spatial location of these paths, which, in turn, aids in the spatial location of any defect (e.g. dental caries) in the tooth 40. Both one-dimensional and two-dimensional arrays can be setup as phased arrays.

Figure 12:
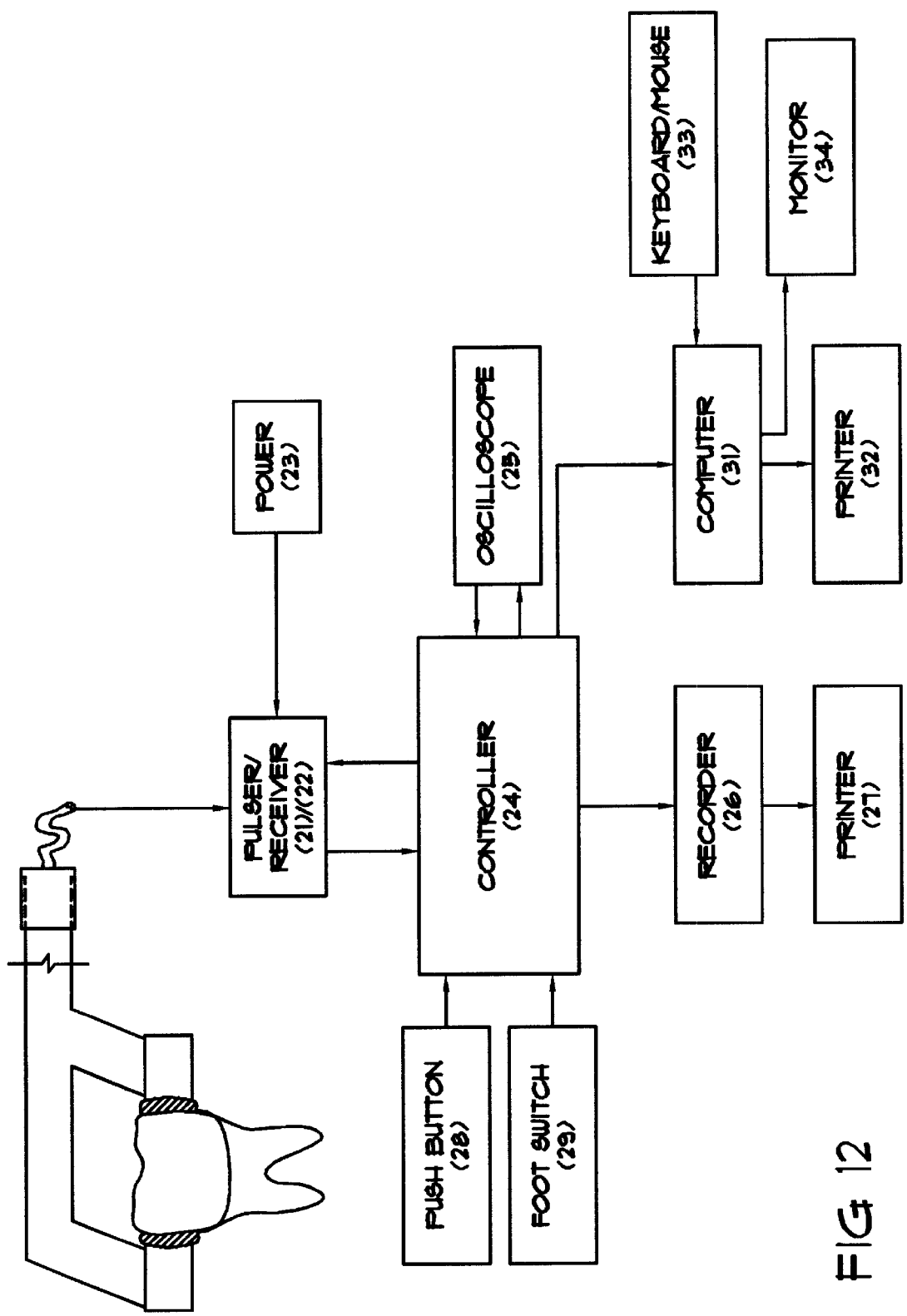
FIG. 12 illustrates the fifth to the tenth embodiment of the transducer system with a block diagram of peripheral electrical and/or electronic components.

In another preferred embodiment FIG. 12 shows an array transducer system 14, 15, embodiment five through eight, may be networked to peripheral electronic and/or electrical components. This illustrates schematically one example of the relationship between said array transducer system 14, 15 and peripheral components for at least some of the corresponding embodiments of said transducer system 14, 15. A pulser (signal generator) 21 producing a suitable electronic ultrasonic stress wave is electrically interconnected to the transmitting transducer that is then able to impart ultrasonic stress waves through the tooth 40 as hereinbefore described. Stress waves are received by one or more receiving transducers in the array on the opposite side of the tooth 40. If a single receiving transducer is selected to receive the stress wave it can be any in the set of receiving transducers in the receiving array. Each transducer in the receiving array is treated as a separate channel and will have its own peripheral electronic and/or electrical components or a separate channel in the associated peripheral electronic and/or electrical components. Stress waves received by the receiving transducer are converted into corresponding electrical signals that are then amplified and processed in a processor 22.

Peripheral electronic means such as an oscilloscope 25 can be operatively networked to the processor 22 and may be used for displaying the profile of said stress waves received by said the receiving transducer 14 in a manner known in the art. Said electrical signals may also be channeled to an electronic computer 31 for further analysis. For each receive channel the said oscilloscope 25 may typically display a receive pulse waveform (FIG. 15). The receive pulse waveform represented by the transmission time displayed on the oscilloscope 25 is formed of many parts. Transmission time is the time it takes for the stress (acoustic) wave to travel from the transmitting transducer to the receiving transducer. Due to the complex paths the stress wave can take through the various structures of the tooth 40, there is a transmission time for every possible path. The shortest path in time is not necessarily the shortest path in space. The stress wave may travel further in a higher velocity enamel layer and yet arrive sooner than the wave that travels a shorter path through the lower velocity dentine layer. Due to the many possible paths through the tooth 40, the stress wave transmitted by the transmit transducer will result in many waves, separated in time, at the receive transducer. For our purposes, transmission time represents the time it takes for the first stress wave to reach the transducer. This time represents the shorted stress (acoustic) path in time through the tooth 40. Each time the transducer system is moved, either manually, mechanically the transmission time displayed on the oscilloscope 25 will be different. With suitable analysis, a system will be able to identify dental lesions 41 and other defects by analyzing the different transmission times and the resulting waveforms. The received stress wave electrical signals may also be channeled to an electronic computer 31 for further analysis. If a computer 31 is used there will be either pushbuttons 29 on the handling device 2, 4 or footswitches 28 for the transducer system that will signal the computer 31 when to record 26 the received stress wave waveform so it can be processed and/or be viewed or printed 27 latter. This system can be further enhanced by processing the information from all the receive transducers in the receive array for each transmit pulse to show the tomography of each structure or layer in the tooth 40.

When a horizontal or vertical array transducer system 14, 15 is used the transducer system will have to be moved (translated), either mechanically, this could be done by a motorized system using stepping motors or gear motors or electrically as in a phased array, after the stress wave pulse information is viewed or recorded.

For a horizontal array transducer system 14 will be moved vertically on the tooth 40. Typically the horizontal array transducer system 14 will be placed near the top of the crown for the first reading. Once the tooth 40 is viewed or recorded the horizontal array transducer system 14 will be moved towards the gum line 45 a set amount and the process will be repeated. It can be repeated clear down onto the gum 45 itself. This process will be continued until the whole area to be surveyed is covered. If the only area of concern is the gum 45 area it would be possible to do a survey of that area alone. By using a digital oscilloscope 25 and saving waveforms it is possible to view and compare each slice of the tooth 40 recorded this way. From this information it is possible to diagnose secondary lesions and other defects in a tooth 40 or under a gold crown 42. It is also possible to diagnose gingivitis and other periodontal diseases.

For a vertical array transducer system 15 will be moved horizontally across the tooth 40. Typically the vertical array transducer system 15 will be placed vertically at one side of the tooth 40 with one pair of opposing transducers near the top of the crown for the first reading. Once the tooth 40 is viewed or recorded the vertical array transducer system 15 will be moved towards the other side of the tooth 40 in a set amount and the process will be repeated until the whole tooth 40 is surveyed. The vertical array transducer system can be placed on the gum 45 if that area is the only point of interest. By using a digital oscilloscope 25 and saving images it is possible to view and compare each slice of the tooth 40 recorded this way. From this information it is possible to diagnose secondary lesions and other defects in a tooth 40 or under a gold crown 42. It is also possible to diagnose gingivitis and other periodontal.

When there is a horizontal and vertical array transducer system 16 it is possible, as is the art, to have a representation displayed on the monitor 34, without the need for mechanical translation, showing the tooth 40 as a whole as well as a representation of all its interior structures shown in different colors to include all dental lesions 41 and other defects. When the horizontal and vertical array transducer system 16 is placed over the tooth 40 to be diagnosed and its related gum tissue the image produced will allow for the diagnoses of secondary lesions and other defects in a tooth 40 or under a gold crown 42 as well as of gingivitis and other periodontal diseases will be seen plainly. Depending on the design of the horizontal and vertical array transducer system 16 it might be necessary to move it in set amount to get a total picture with separate images being, as is the art, "stitched" together.

Figure 13:
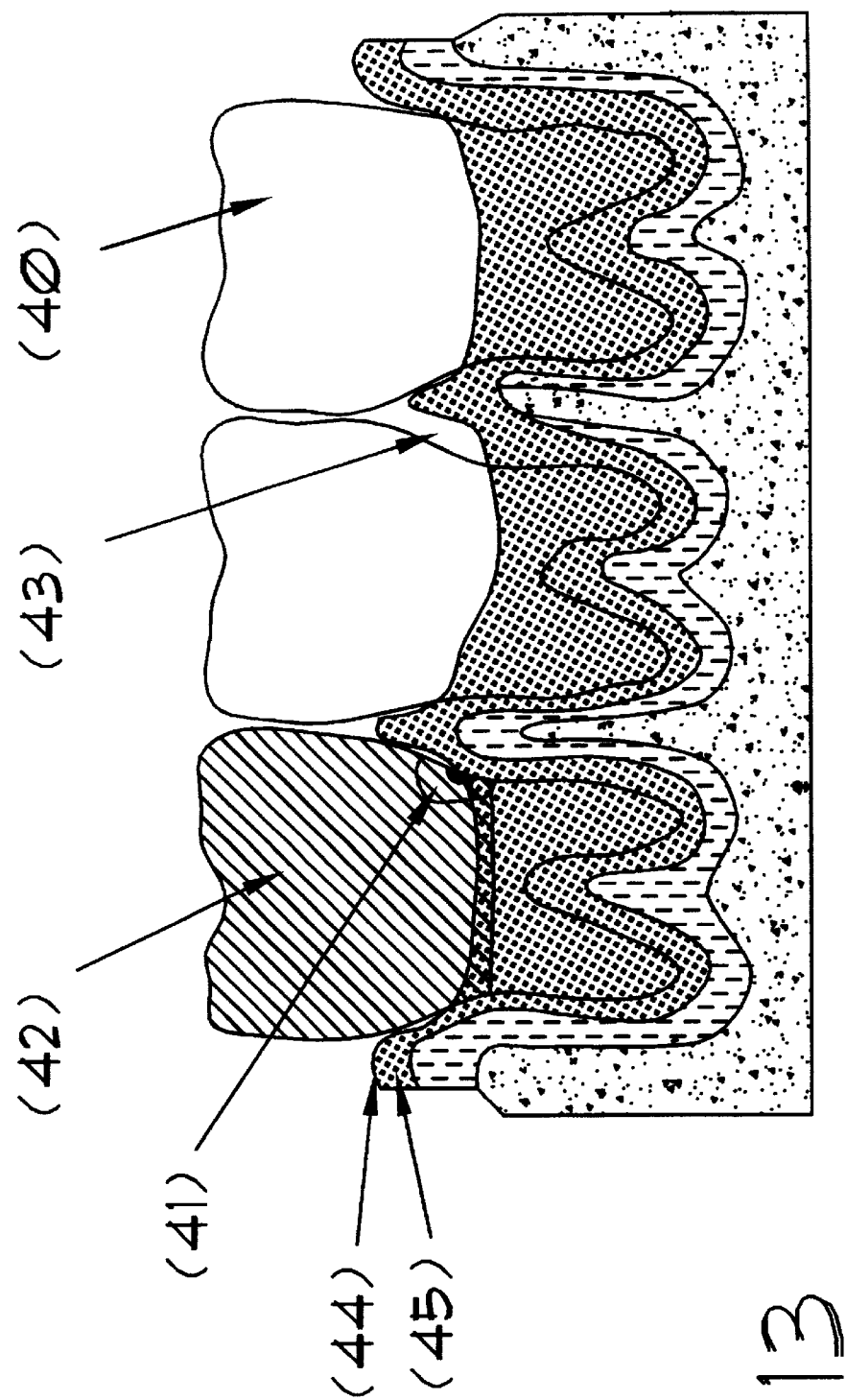
FIG. 13 illustrates in detail a picture of a tooth with a gold crown with secondary lesions under the crown and a periodontal pocket and interfaces that can be shown and/or mapped by the invention.

FIG. 13 illustrates in detail a picture of a tooth 40 with a gold crown 42 with dental lesions 41 under the crown and a periodontal pocket 43 and interfaces that can be shown and/or mapped by the invention.

Figure 14:
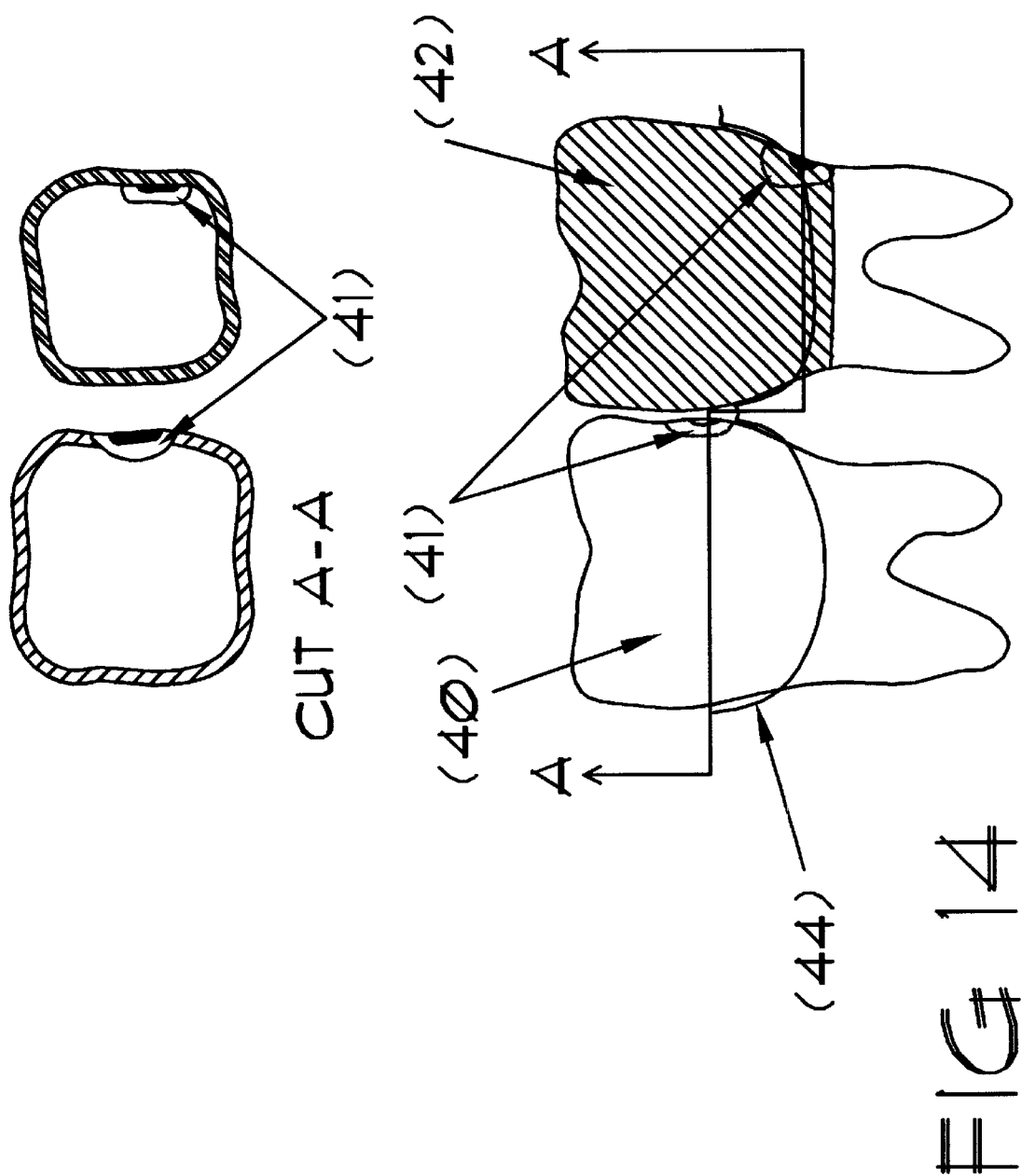
FIG. 14 illustrates in detail a picture of teeth with an interproximal dental lesions that can be shown and/or mapped by the invention.

FIG. 14 illustrates in detail a section of a dentition comprising a number of adjacent teeth with surface dental lesions 41 and interproximal dental lesions 41 that can be shown and/or mapped by the invention.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for determining the location of primary dental caries in a tooth comprising: generating a stress wave by means of a stress wave source; transmitting said stress wave through a tooth from one side thereof; receiving said stress wave at an opposite side of the tooth and converting said stress wave into an electrical signal; using said electrical signal to measure the transmission time of said stress wave through the tooth and; interpreting said transmission time to determine the location of primary dental caries in the tooth.

2. The method of claim 1 wherein said stress wave is generated, transmitted and converted by a pair of transducers placed opposite one another, on opposite sides of the tooth, and in approximation to the tooth.

3. The method of claim 1 wherein said stress wave is generated, transmitted and converted by a pair of focused transducers collinearly placed opposite each other and in approximation to the tooth, said transducers being placed on opposite sides of the tooth, and spaced apart such that their focal points substantially coincide.

4. The method of claim 1 wherein said stress wave is generated, transmitted and converted by a pair of transducers placed opposite each other, on opposite sides of the tooth and in approximation to the tooth, said transducers having a connecting bridge to maintain their alignment.

5. The method of claim 1 wherein said stress wave is generated, transmitted and converted by a pair of focused transducers collinearly placed opposite each other and in approximation to the tooth, said transducers being placed on opposite sides of the tooth, and spaced apart such that their focal points substantially coincide, said transducers having a connecting bridge to maintain their alignment.

6. The method of claim 1 wherein said stress wave is generated, transmitted and converted by a pair of horizontal arrays of transducers placed opposite each other and in approximation to the tooth, said arrays being planar and located on opposite sides of the tooth.

7. The method of claim 1 wherein said stress wave is generated, transmitted and converted by a pair of horizontal arrays of transducers placed opposite each other and in approximation to the tooth, said arrays being curvilinear and located on the same horizontal plane on opposite sides of the tooth.

8. The method of claim 1 wherein said stress wave is generated, transmitted and converted by a pair of horizontal arrays of focused transducers collinearly placed opposite each other and in approximation to the tooth, said arrays being planar, located on opposite sides of the tooth, and spaced apart such that their focal points substantially coincide.

9. The method of claim 1 wherein said stress wave is generated, transmitted and converted by a pair of horizontal arrays of focused transducers collinearly placed opposite each other and in approximation to the tooth, said arrays being curvilinear, located on the same horizontal plane on opposite sides of the tooth, and spaced apart such that their focal point substantially coincide.

10. The method of claim 1 wherein said stress wave is generated, transmitted and converted by a pair of vertical arrays of transducers placed opposite each other and in approximation to the tooth, said arrays being planar and located on opposite sides of the tooth.

11. The method of claim 1 wherein said stress wave is generated, transmitted and converted by a pair of vertical arrays of transducers placed opposite each other and in approximation to the tooth, said arrays being curvilinear and located on the same vertical plane on opposite sides of the tooth.

12. The method of claim 1 wherein said stress wave is generated, transmitted and converted by a pair of vertical arrays of focused transducers collinearly placed opposite each other and in approximation to the tooth, said arrays being planar, located on opposite sides of the tooth, and spaced apart such that their focal point substantially coincide.

13. The method of claim 1 wherein said stress wave is generated, transmitted and converted by a pair of vertical arrays of focused transducers collinearly placed opposite each other in approximation to the tooth, said arrays being curvilinear, located on the same vertical plane on opposite sides of the tooth, and spaced apart such that their focal points coincide.

14. The method of claim 1 wherein said stress wave is generated, transmitted and converted by a pair of horizontal and vertical arrays of transducers placed opposite each other and in approximation to the tooth, said arrays being planar and located on opposite sides of the tooth.

15. The method of claim 1 wherein said stress wave is generated, transmitted and converted by a pair of horizontal and vertical arrays of transducers placed opposite each other and in approximation to the tooth, said arrays being curvilinear and located on the same horizontal and vertical planes on opposite sides of the tooth.

16. The method of claim 1 wherein said stress wave is generated, transmitted and converted by a pair of horizontal and vertical arrays of focused transducers collinearly placed opposite each other and in approximation to the tooth, said arrays being planar, located on opposite sides of the tooth and spaced apart such that their focal points substantially coincide.

17. The method of claim 1 wherein said stress wave is generated, transmitted and converted by a pair of horizontal and vertical arrays of focused transducers collinearly placed opposite each other in approximation to the tooth, said arrays being curvilinear, located on the same horizontal and vertical planes on opposite sides of the tooth and spaced apart such that their focal points substantially coincide.

18. The method of claim 1 wherein the measurement of transmission time is made using a threshold detector.

19. The method of claim 18 wherein the measurement of transmission time is made on the first derivative of the envelope of the stress wave.

20. The method of claim 18 wherein the measurement of transmission time is made on the correlation signal produced by the correlation of the received stress wave with the transmitted stress signal.

21. The method of claim 1 wherein the measurement of transmission time is made using a peak detector.

22. The method of claim 21 wherein the measurement of transmission time is made on the first derivative of the envelope of the stress wave.

23. The method of claim 21 wherein the measurement of transmission time is made on the correlated signal produced by the correlation of the received stress wave with the transmitted stress signal.

24. The method of claim 1 wherein the location of primary dental caries is determined by an anomalous change in the transmission time.

25. A method for determining the extent of primary dental caries in a tooth comprising: generating a stress wave by means of a stress wave source; transmitting said stress wave through a tooth from one side thereof; receiving said stress wave at an opposite side of the tooth and converting said stress wave into an electrical signal; using said electrical signal to measure the transmission time of said stress wave through the tooth and; interpreting said transmission time to determine the extent of primary dental caries in the tooth.

26. The method of claim 25 wherein said stress wave is generated, transmitted and converted by a pair of transducers placed opposite one another, on opposite sides of the tooth, and in approximation to the tooth.

27. The method of claim 25 wherein said stress wave is generated, transmitted and converted by a pair of focused transducers collinearly placed opposite each other and in approximation to the tooth, said transducers being placed on opposite sides of the tooth, and spaced apart such that their focal points substantially coincide.

28. The method of claim 25 wherein said stress wave is generated, transmitted and converted by a pair of transducers placed opposite each other, on opposite sides of the tooth and in approximation to the tooth, said transducers having a connecting bridge to maintain their alignment.

29. The method of claim 25 wherein said stress wave is generated, transmitted and converted by a pair of focused transducers collinearly placed opposite each other and in approximation to the tooth, said transducers being placed on opposite sides of the tooth, and spaced apart such that their focal points substantially coincide, said transducers having a connecting bridge to maintain their alignment.

30. The method of claim 25 wherein said stress wave is generated, transmitted and converted by a pair of horizontal arrays of transducers placed opposite each other and in approximation to the tooth, said arrays being planar and located on opposite sides of the tooth.

31. The method of claim 25 wherein said stress wave is generated, transmitted and converted by a pair of horizontal arrays of transducers placed opposite each other and in approximation to the tooth, said arrays being curvilinear and located on the same horizontal plane on opposite sides of the tooth.

32. The method of claim 25 wherein said stress wave is generated, transmitted and converted by a pair of horizontal arrays of focused transducers collinearly placed opposite each other and in approximation to the tooth, said arrays being planar, located on opposite sides of the tooth, and spaced apart such that their focal points substantially coincide.

33. The method of claim 25 wherein said stress wave is generated, transmitted and converted by a pair of horizontal arrays of focused transducers collinearly placed opposite each other and in approximation to the tooth, said arrays being curvilinear, located on the same horizontal plane on opposite sides of the tooth, and spaced apart such that their focal point substantially coincide.

34. The method of claim 25 wherein said stress wave is generated, transmitted and converted by a pair of vertical arrays of transducers placed opposite each other and in approximation to the tooth, said arrays being planar and located on opposite sides of the tooth.

35. The method of claim 25 wherein said stress wave is generated, transmitted and converted by a pair of vertical arrays of transducers placed opposite each other and in approximation to the tooth, said arrays being curvilinear and located on the same vertical plane on opposite sides of the tooth.

36. The method of claim 25 wherein said stress wave is generated, transmitted and converted by a pair of vertical arrays of focused transducers collinearly placed opposite each other and in approximation to the tooth, said arrays being planar, located on opposite sides of the tooth, and spaced apart such that their focal point substantially coincide.

37. The method of claim 25 wherein said stress wave is generated, transmitted and converted by a pair of vertical arrays of focused transducers collinearly placed opposite each other in approximation to the tooth, said arrays being curvilinear, located on the same vertical plane on opposite sides of the tooth, and spaced apart such that their focal points coincide.

38. The method of claim 25 wherein said stress wave is generated, transmitted and converted by a pair of horizontal and vertical arrays of transducers placed opposite each other and in approximation to the tooth, said arrays being planar and located on opposite sides of the tooth.

39. The method of claim 25 wherein said stress wave is generated, transmitted and converted by a pair of horizontal and vertical arrays of transducers placed opposite each other and in approximation to the tooth, said arrays being curvilinear and located on the same horizontal and vertical planes on opposite sides of the tooth.

40. The method of claim 26 wherein said stress wave is generated, transmitted and converted by a pair of horizontal and vertical arrays of focused transducers collinearly placed opposite each other and in approximation to the tooth, said arrays being planar, located on opposite sides of the tooth and spaced apart such that their focal points substantially coincide.

41. The method of claim 25 wherein said stress wave is generated, transmitted and converted by a pair of horizontal and vertical arrays of focused transducers collinearly placed opposite each other in approximation to the tooth, said arrays being curvilinear, located on the same horizontal and vertical planes on opposite sides of the tooth and spaced apart such that their focal points substantially coincide.

42. The method of claim 25 wherein the measurement of transmission time is made using a threshold detector.

43. The method of claim 42 wherein the measurement of transmission time is made on the first derivative of the envelope of the stress wave.

44. The method of claim 42 wherein the measurement of transmission time is made on the correlation signal produced by the correlation of the received stress wave with the transmitted stress signal.

45. The method of claim 25 wherein the measurement of transmission time is made using a peak detector.

46. The method of claim 45 wherein the measurement of transmission time is made on the first derivative of the envelope of the stress wave.

47. The method of claim 45 wherein the measurement of transmission time is made on the correlated signal produced by the correlation of the received stress wave with the transmitted stress signal.

48. The method of claim 25 wherein the extent of primary dental caries is determined by an anomalous change in the transmission time.

49. A method for determining the location of secondary dental caries in a tooth comprising: generating a stress wave by means of a stress wave source; transmitting said stress wave through a tooth from one side thereof; receiving said stress wave at an opposite side of the tooth and converting said stress wave into an electrical signal; using said electrical signal to measure the transmission time of said stress wave through the tooth and; interpreting said transmission time to determine the location of secondary dental caries in the tooth.

50. The method of claim 49 wherein said stress wave is generated, transmitted and converted by a pair of transducers placed opposite one another, on opposite sides of the tooth, and in approximation to the tooth.

51. The method of claim 49 wherein said stress wave is generated, transmitted and converted by a pair of focused transducers collinearly placed opposite each other and in approximation to the tooth, said transducers being placed on opposite sides of the tooth, and spaced apart such that their focal points substantially coincide.

52. The method of claim 49 wherein said stress wave is generated, transmitted and converted by a pair of transducers placed opposite each other, on opposite sides of the tooth and in approximation to the tooth, said transducers having a connecting bridge to maintain their alignment.

53. The method of claim 49 wherein said stress wave is generated, transmitted and converted by a pair of focused transducers collinearly placed opposite each other and in approximation to the tooth, said transducers being placed on opposite sides of the tooth, and spaced apart such that their focal points substantially coincide, said transducers having a connecting bridge to maintain their alignment.

54. The method of claim 49 wherein said stress wave is generated, transmitted and converted by a pair of horizontal arrays of transducers placed opposite each other and in approximation to the tooth, said arrays being planar and located on opposite sides of the tooth.

55. The method of claim 49 wherein said stress wave is generated, transmitted and converted by a pair of horizontal arrays of transducers placed opposite each other and in approximation to the tooth, said arrays being curvilinear and located on the same horizontal plane on opposite sides of the tooth.

56. The method of claim 49 wherein said stress wave is generated, transmitted and converted by a pair of horizontal arrays of focused transducers collinearly placed opposite each other and in approximation to the tooth, said arrays being planar, located on opposite sides of the tooth, and spaced apart such that their focal points substantially coincide.

57. The method of claim 49 wherein said stress wave is generated, transmitted and converted by a pair of horizontal arrays of focused transducers collinearly placed opposite each other and in approximation to the tooth, said arrays being curvilinear, located on the same horizontal plane on opposite sides of the tooth, and spaced apart such that their focal point substantially coincide.

58. The method of claim 49 wherein said stress wave is generated, transmitted and converted by a pair of vertical arrays of transducers placed opposite each other and in approximation to the tooth, said arrays being planar and located on opposite sides of the tooth.

59. The method of claim 49 wherein said stress wave is generated, transmitted and converted by a pair of vertical arrays of transducers placed opposite each other and in approximation to the tooth, said arrays being curvilinear and located on the same vertical plane on opposite sides of the tooth.

60. The method of claim 49 wherein said stress wave is generated, transmitted and converted by a pair of vertical arrays of focused transducers collinearly placed opposite each other and in approximation to the tooth, said arrays being planar, located on opposite sides of the tooth, and spaced apart such that their focal point substantially coincide.

61. The method of claim 49 wherein said stress wave is generated, transmitted and converted by a pair of vertical arrays of focused transducers collinearly placed opposite each other in approximation to the tooth, said arrays being curvilinear, located on the same vertical plane on opposite sides of the tooth, and spaced apart such that their focal points coincide.

62. The method of claim 49 wherein said stress wave is generated, transmitted and converted by a pair of horizontal and vertical arrays of transducers placed opposite each other and in approximation to the tooth, said arrays being planar and located on opposite sides of the tooth.

63. The method of claim 49 wherein said stress wave is generated, transmitted and converted by a pair of horizontal and vertical arrays of transducers placed opposite each other and in approximation to the tooth, said arrays being curvilinear and located on the same horizontal and vertical planes on opposite sides of the tooth.

64. The method of claim 49 wherein said stress wave is generated, transmitted and converted by a pair of horizontal and vertical arrays of focused transducers collinearly placed opposite each other and in approximation to the tooth, said arrays being planar, located on opposite sides of the tooth and spaced apart such that their focal points substantially coincide.

65. The method of claim 49 wherein said stress wave is generated, transmitted and converted by a pair of horizontal and vertical arrays of focused transducers collinearly placed opposite each other in approximation to the tooth, said arrays being curvilinear, located on the same horizontal and vertical planes on opposite sides of the tooth and spaced apart such that their focal points substantially coincide.

66. The method of claim 49 wherein the measurement of transmission time is made using threshold detector.

67. The method of claim 66 wherein the measurement of transmission time is made on the first derivative of the envelope of the stress wave.

68. The method of claim 66 wherein the measurement of transmission time is made on the correlation signal produced by the correlation of the received stress wave with the transmitted stress signal.

69. The method of claim 49 wherein the measurement of transmission time is made using a peak detector.

70. The method of claim 69 wherein the measurement of transmission time is made on the first derivative of the envelope of the stress wave.

71. The method of claim 69 wherein the measurement of transmission time is made on the correlated signal produced by the correlation of the received stress wave with the transmitted stress signal.

72. The method of claim 49 wherein the location of secondary dental caries is determined by an anomalous change in the transmission time.

73. A method for determining the extent of secondary dental caries in a tooth comprising: generating a stress wave by means of a stress wave source; transmitting said stress wave through a tooth from one side thereof; receiving said stress wave at an opposite side of the tooth and converting said stress wave into an electrical signal; using said electrical signal to measure the transmission time of said stress wave through the tooth and; interpreting said transmission time to determine the extent of dental caries in the tooth.

74. The method of claim 73 wherein said stress wave is generated, transmitted and converted by a pair of transducers placed opposite one another, on opposite sides of the tooth, and in approximation to the tooth.

75. The method of claim 73 wherein said stress wave is generated, transmitted and converted by a pair of focused transducers collinearly placed opposite each other and in approximation to the tooth, said transducers being placed on opposite sides of the tooth, and spaced apart such that their focal points substantially coincide.

76. The method of claim 73 wherein said stress wave is generated, transmitted and converted by a pair of transducers placed opposite each other, on opposite sides of the tooth and in approximation to the tooth, said transducers having a connecting bridge to maintain their alignment.

77. The method of claim 73 wherein said stress wave is generated, transmitted and converted by a pair of focused transducers collinearly placed opposite each other and in approximation to the tooth, said transducers being placed on opposite sides of the tooth, and spaced apart such that their focal points substantially coincide, said transducers having a connecting bridge to maintain their alignment.

78. The method of claim 73 wherein said stress wave is generated, transmitted and converted by a pair of horizontal arrays of transducers placed opposite each other and in approximation to the tooth, said arrays being planar and located on opposite sides of the tooth.

79. The method of claim 73 wherein said stress wave is generated, transmitted and converted by a pair of horizontal arrays of transducers placed opposite each other and in approximation to the tooth, said arrays being curvilinear and located on the same horizontal plane on opposite sides of the tooth.

80. The method of claim 73 wherein said stress wave is generated, transmitted and converted by a pair of horizontal arrays of focused transducers collinearly placed opposite each other and in approximation to the tooth, said arrays being planar, located on opposite sides of the tooth, and spaced apart such that their focal points substantially coincide.

81. The method of claim 73 wherein said stress wave is generated, transmitted and converted by a pair of horizontal arrays of focused transducers collinearly placed opposite each other and in approximation to the tooth, said arrays being curvilinear, located on the same horizontal plane on opposite sides of the tooth, and spaced apart such that their focal point substantially coincide.

82. The method of claim 73 wherein said stress wave is generated, transmitted and converted by a pair of vertical arrays of transducers placed opposite each other and in approximation to the tooth, said arrays being planar and located on opposite sides of the tooth.

83. The method of claim 73 wherein said stress wave is generated, transmitted and converted by a pair of vertical arrays of transducers placed opposite each other and in approximation to the tooth, said arrays being curvilinear and located on the same vertical plane on opposite sides of the tooth.

84. The method of claim 73 wherein said stress wave is generated, transmitted and converted by a pair of vertical arrays of focused transducers collinearly placed opposite each other and in approximation to the tooth, said arrays being planar, located on opposite sides of the tooth, and spaced apart such that their focal point substantially coincide.

85. The method of claim 73 wherein said stress wave is generated, transmitted and converted by a pair of vertical arrays of focused transducers collinearly placed opposite each other in approximation to the tooth, said arrays being curvilinear, located on the same vertical plane on opposite sides of the tooth, and spaced apart such that their focal points coincide.

86. The method of claim 73 wherein said stress wave is generated, transmitted and converted by a pair of horizontal and vertical arrays of transducers placed opposite each other and in approximation to the tooth, said arrays being planar and located on opposite sides of the tooth.

87. The method of claim 73 wherein said stress wave is generated, transmitted and converted by a pair of horizontal and vertical arrays of transducers placed opposite each other and in approximation to the tooth, said arrays being curvilinear and located on the same horizontal and vertical planes on opposite sides of the tooth.

88. The method of claim 73 wherein said stress wave is generated, transmitted and converted by a pair of horizontal and vertical arrays of focused transducers collinearly placed opposite each other and in approximation to the tooth, said arrays being planar, located on opposite sides of the tooth and spaced apart such that their focal points substantially coincide.

89. The method of claim 73 wherein said stress wave is generated, transmitted and converted by a pair of horizontal and vertical arrays of focused transducers collinearly placed opposite each other in approximation to the tooth, said arrays being curvilinear, located on the same horizontal and vertical planes on opposite sides of the tooth and spaced apart such that their focal points substantially coincide.

90. The method of claim 73 wherein the measurement of transmission time is made using a threshold detector.

91. The method of claim 90 wherein the measurement of transmission time is made on the first derivative of the envelope of the stress wave.

92. The method of claim 90 wherein the measurement of transmission time is made on the correlation signal produced by the correlation of the received stress wave with the transmitted stress signal.

93. The method of claim 73 wherein the measurement of transmission time is made using a peak detector.

94. The method of claim 93 wherein the measurement of transmission time is made on the first derivative of the envelope of the stress wave.

95. The method of claim 93 wherein the measurement of transmission time is made on the correlated signal produced by the correlation of the received stress wave with the transmitted stress signal.

96. The method of claim 73 wherein the extent of secondary dental caries is determined by an anomalous change in the transmission time.

* * * * *